US010407411B2

(12) United States Patent
Morra et al.

(10) Patent No.: US 10,407,411 B2
(45) Date of Patent: Sep. 10, 2019

(54) PURIFIED CENICRIVIROC AND PURIFIED INTERMEDIATES FOR MAKING CENICRIVIROC

(71) Applicant: Tobira Therapeutics, Inc., Parsippany, NJ (US)

(72) Inventors: Nicholas Morra, Parsippany, NJ (US); Pasit Phiasivongsa, Parsippany, NJ (US)

(73) Assignee: Tobira Therapeutics, Inc., Parsipanny, NJ (US)

(*) Notice: Subject to any disclaimer, the term of this patent is extended or adjusted under 35 U.S.C. 154(b) by 0 days.

(21) Appl. No.: 15/628,968

(22) Filed: Jun. 21, 2017

(65) Prior Publication Data

US 2017/0362207 A1 Dec. 21, 2017

Related U.S. Application Data

(60) Provisional application No. 62/352,885, filed on Jun. 21, 2016.

(51) Int. Cl.
*C07D 225/06* (2006.01)
*C07D 403/12* (2006.01)
*B01J 31/22* (2006.01)
*B01J 31/24* (2006.01)

(52) U.S. Cl.
CPC ........ *C07D 403/12* (2013.01); *B01J 31/2208* (2013.01); *B01J 31/2404* (2013.01)

(58) Field of Classification Search
CPC .................................................. C07D 225/06
See application file for complete search history.

(56) References Cited

U.S. PATENT DOCUMENTS

| | | | |
|---|---|---|---|
| 7,371,772 | B2 | 5/2008 | Shiraishi et al. |
| 8,183,273 | B2 | 5/2012 | Shiraishi et al. |
| 8,362,058 | B2 | 1/2013 | Shiraishi et al. |
| 8,741,943 | B2 | 6/2014 | Shiraishi et al. |
| 2004/0259876 | A1 | 12/2004 | Shiraishi et al. |
| 2005/0107606 | A1 | 5/2005 | Tawada et al. |
| 2008/0031942 | A1 | 2/2008 | Uchiyama et al. |
| 2008/0161287 | A1 | 7/2008 | Shiraishi et al. |
| 2008/0234343 | A1 | 9/2008 | Yoshinari |
| 2008/0249147 | A1 | 10/2008 | Yoshinari |
| 2009/0030032 | A1 | 1/2009 | Shiraishi et al. |
| 2012/0232028 | A1 | 9/2012 | Shiraishi et al. |
| 2016/0008326 | A1 | 1/2016 | Shiraishi et al. |
| 2016/0081985 | A1 | 3/2016 | Menning et al. |

FOREIGN PATENT DOCUMENTS

| | | | |
|---|---|---|---|
| CA | 2607992 | * 2/2003 | ........... C07D 403/12 |
| EP | 1889839 A1 | 2/2008 | |
| JP | 62-265270 A | 11/1987 | |
| WO | WO 1996/001267 A1 | 1/1996 | |
| WO | WO 1999/032100 A2 | 7/1999 | |
| WO | WO 2000/010965 A2 | 3/2000 | |
| WO | WO 2001/017947 A1 | 3/2001 | |
| WO | WO 2003/014105 A1 | 2/2003 | |
| WO | WO 2003/076411 A1 | 9/2003 | |
| WO | WO 2012/068366 A2 | 5/2012 | |
| WO | WO 2014/186581 A1 | 11/2014 | |
| WO | WO 2015/143367 A2 | 9/2015 | |
| WO | WO 2016/105527 A1 | 6/2016 | |
| WO | WO 2016/130179 A1 | 8/2016 | |

OTHER PUBLICATIONS

Salmas et al., "Investigation of Inhibition Mechanism of Chemokine Receptor CCR5 by Micro-second Molecular Dynamics Simulations." Scientific Reports (2015); 5: 13180.
PCT/JP2002/008043, International Preliminary Examination Report dated Nov. 7, 2003, 38 pages.
PCT/JP2002/008043, International Search Report dated Nov. 11, 2002, 4 pages.
PCT/US2015/000289, International Search Report and Written Opinion dated Apr. 12, 2016, 16 pages.
PCT/US2015/000289, International Preliminary Report on Patentability dated Jun. 27, 2017, 12 pages.
Baba, M., et al., "A small-molecule, nonpeptide CCR5 antagonist with highly potent and selective anti-HIV-1 activity," Proc. Natl. Acad Sci. USA (1999); 96: 5698-5703.
Baba, M., et al., "TAK-652 Inhibits CCR5-Mediated Human Immunodeficiency Virus Type 1 Infection In Vitro and Has Favorable Pharmacokinetics in Humans," Antimicrobial Agents and Chemotherapy (2005); 49(11): 4584-4591.
Dawson, T. C., et al. "Absence of CC chemokine receptor-2 reduces atherosclerosis in apolipoprotein E-deficient mice," Atherosclerosis (1999); 143: 205-211.
Fischereder, M., et al., "CC chemokine receptor 5 and renal-transplant survival," The Lancet (2001); 357: 1758-1761.
Fukushi et al., "Synthesis and Platelet-Activating Factor (PAF)-Antagonistic Activities of 1,4-Disubstituted Piperazine Derivatives," Chem. Pharm. Bull. (1994); 42(3): 541-550.
Horuk, R., "Chemokine receptors," Cytokine and Growth Factor Reviews (2001); 12(4): 313-335.
Kazmierski, W., et al., "Recent Progress in Discovery of Small-Molecule CCR5 Chemokine Receptor Ligands as HIV-1 Inhibitors," Bioorganic & Medicinal Chemistry (2003), 11: 2663-2676.
Klibanov, Olga M., et al. "Cenicriviroc, an orally active CCR5 antagonist for the potential treatment of HIV infection." Curr Opin Investig Drugs (2010); 11.8: 940-950.
Liu, R., et al., "Homozygous Defect in HIV-1 Coreceptor Accounts for Resistance of Some Multiply-Exposed Individuals to HIV-1 Infection," Cell (1996); 86: 367-377.
Maeda, K., et al. "The current status of and challenges in the development of CCR5 inhibitors as therapeutics for HIV-1 infection," Current Opinion in Pharmacology (2004); 4(5): 447-452.
Pokorny, V., et al., "Evidence for negative association of the chemokine receptor CCR5 d32 polymorphism with rheumatoid arthritis," Ann. Rheum. Dis. (2005); 64: 487-490.

(Continued)

*Primary Examiner* — Noble E Jarrell
(74) *Attorney, Agent, or Firm* — Mintz Levin Cohn Ferris Glovsky and Popeo, P.C.

(57) ABSTRACT

The disclosure includes high purity compounds having CCR5 and/or CCR2 antagonism, or salts thereof, high purity intermediates thereto and processes for synthesizing the same.

16 Claims, 3 Drawing Sheets

(56) References Cited

OTHER PUBLICATIONS

Princen, K. et al. "HIV chemokine receptor inhibitors as novel anti-HIV drugs", Cytokine & Growth Factor Reviews (2005); 16: 659-677.
Samson, M., et al., "Resistance to HIV-I infection in caucasian individuals bearing mutant alleles ot he CCR-5 chemokine receptor gene," Nature (1996); 382: 722-725.
Sellebjerg, F. et al. "CCR5 Δ32, matrix metalloproteinase-9 and disease activity in multiple sclerosis", Journal of Neuroimmunology (2000); 102(1): 98-106.
Seto, M., et al., "Orally active CCR5 antagonists as anti-HIV-1 agents: synthesis and biological activity of 1-benzothiepine 1,1-dioxide and 1-benzazepine derivatives containing a tertiary amine moiety." Chem Pharm Bull (Tokyo) (2004); 52(5): 577-590.
Seto, M., et al., "Highly Potent and Orally Active CCR5 Antagonists as Anti-HIV-1 Agents: Synthesis and Biological Activities of 1-Benzazocine Derivatives Containing a Sulfoxide Moiety." J. Med. Chem. (2006); 49 (6): 2037-2048.
University of North Carolina School of Medicine, "Case of the Missing Monocyte: Gene Appears to Protect Against Rheumatoid Arthritis," ScienceDaily LLC, United States, Oct. 11, 2011, 3 pages.
Xia et al., "Recent Developments in CCR2 Antagonists." Expert Opinion on Therapeutic Patents (2009); 19(3): 295-303.

\* cited by examiner

PURIFIED CENICRIVIROC AND PURIFIED INTERMEDIATES FOR MAKING CENICRIVIROC

CROSS-REFERENCE TO RELATED APPLICATION

This application claims the benefit of priority to U.S. Provisional Patent Application No. 62/352,885 filed Jun. 21, 2016, the disclosures of which is hereby incorporated by reference in its entirety for all purposes.

FIELD

The present disclosure relates to purified compounds having CCR5 and/or CCR2 antagonism, or a salt thereof, and purified intermediates for making the compounds.

BACKGROUND

It is known that cenicriviroc (CVC) inhibits CCR5 and CCR2 receptors and prevents virus from entering into a human cell, such as the HIV virus (U.S. Pat. No. 8,183,273). The synthesis of CVC is also previously disclosed in U.S. patent application Ser. No. 10/506,955 and Int. Pat. Pub. No. WO 2001017947.

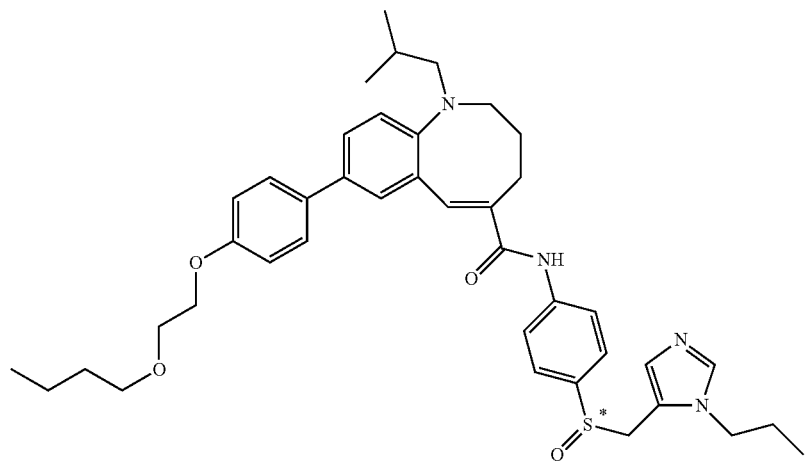

Cenicriviroc

The present disclosure provides for purified CVC, CVC salts, including CVC methane sulfonic acid salt, or related analogs, and purified intermediates for preparing the aforesaid.

Conventional methods of synthesizing CVC, CVC salts, and related analogs, resulted in the presence of undesirable impurities. Thus, there is a need for highly pure CVC, purified intermediates thereto and process of making the same.

SUMMARY OF THE DISCLOSURE

This disclosure is directed to highly purified Compound I, a racemic or optically pure form of CVC, and the formation of its methane sulfonic acid salt (Compound I-MsOH) and highly purified intermediate compound II useful for preparing Compound I, and the process for making them. In some embodiments, Compound I and Compound I-MsOH are racemic. In other embodiments, Compound I and Compound I-MsOH comprises an optically active sulfoxide, such as the (S)-isomer denoted as (S)-Compound I-MsOH.

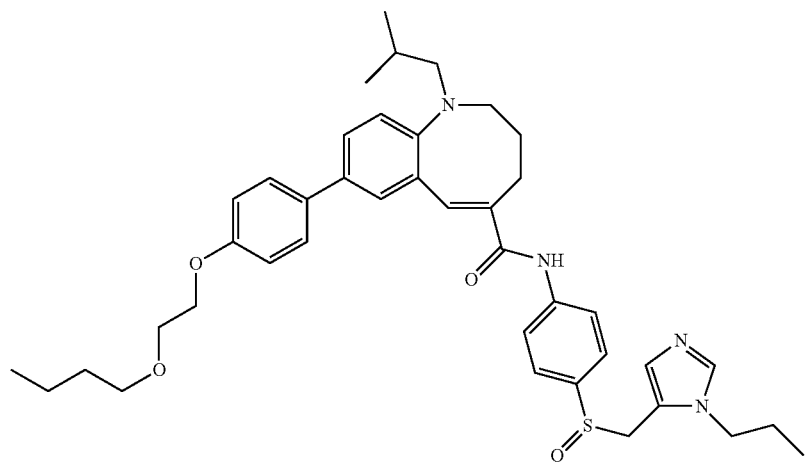
(I)

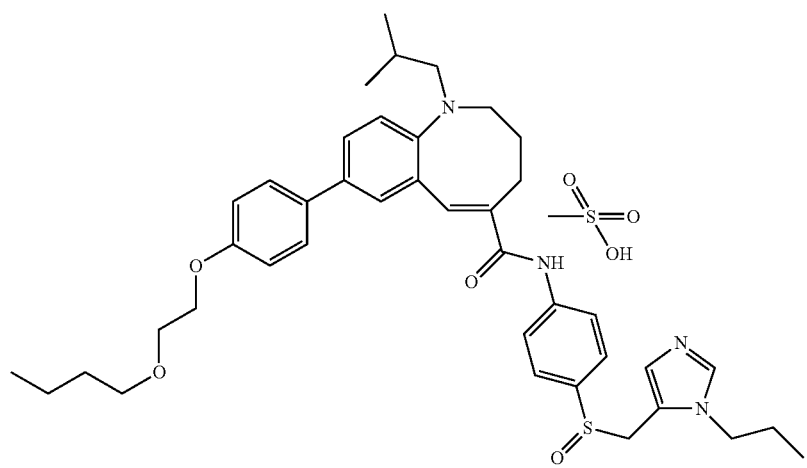
(I-MsOH)

Compound I is synthesized by a reaction between Compound II and Compound III:

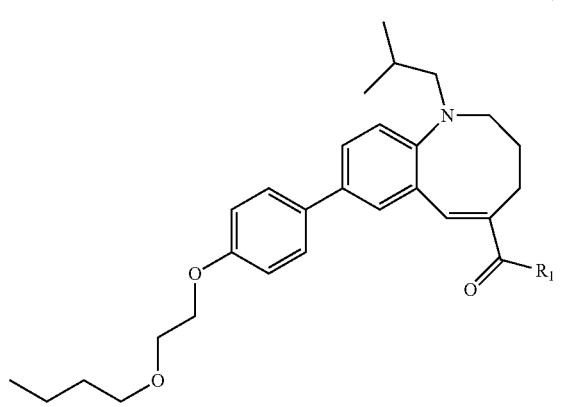
(II)

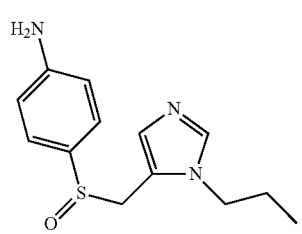
(III)

wherein $R_1$ is selected from the group consisting of H, OH, Cl, Br, $OR_2$, $OCOR_2$, and $NHR_2$; and wherein $R_2$ is selected from the group consisting of H, alkyl, substituted alkyl, aryl, and substituted aryl.

Compound I is synthesized by a reaction between Compound II where $R_1$=OH (Compound II-OH) and Compound III.

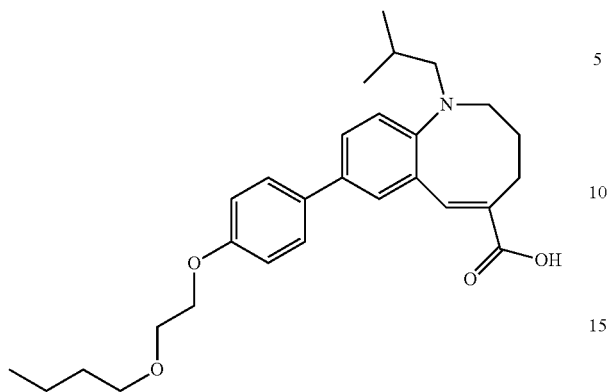

Compound II-OH is synthesized by a reaction between Compound IV and Compound V and/or Compound V-3:

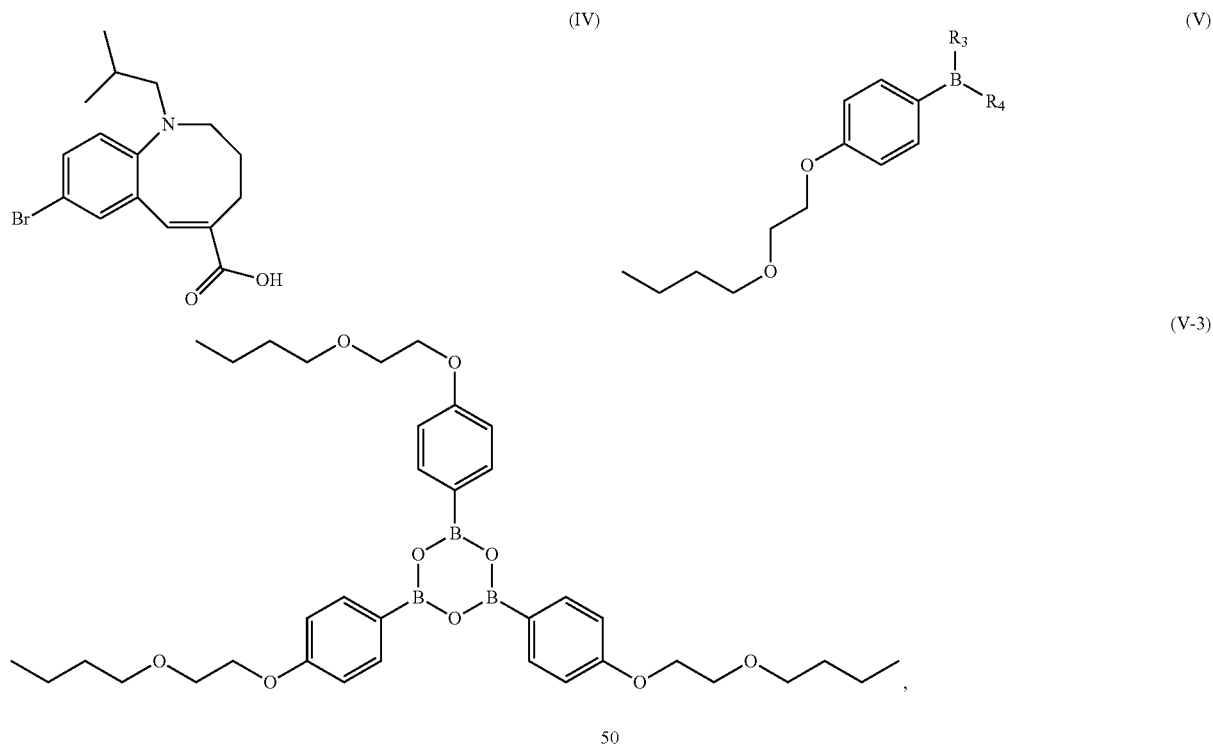

wherein $R_3$ is $Ar_1$ or $OR_5$; $R_4$ is $Ar_2$ or $OR_6$; and $R_5$, and $R_6$ are independently selected from the group consisting of H, alkyl, and substituted alkyl; or $R_5$ and $R_6$ together forms an optionally substituted alkyl or an optionally substituted aryl; $Ar_1$ and $Ar_2$ are independently aryl or substituted aryl.

In some embodiments, $R_3$ and $R_4$ are both OMe or both OH for Compound V, which are denoted as Compound V-OMe or Compound V-OH, respectively.

In some embodiments, Compound V is synthesized from Compound VI.

This disclosure is directed to a process route to minimize impurities represented by Compounds I-MsOH-A, I-MsOH-B, I-MsOH-C, I-MsOH-D, I-MsOH-E, (R)-I-MsOH, VII, VIII, IX, and mesylate esters resulting from MsOH.

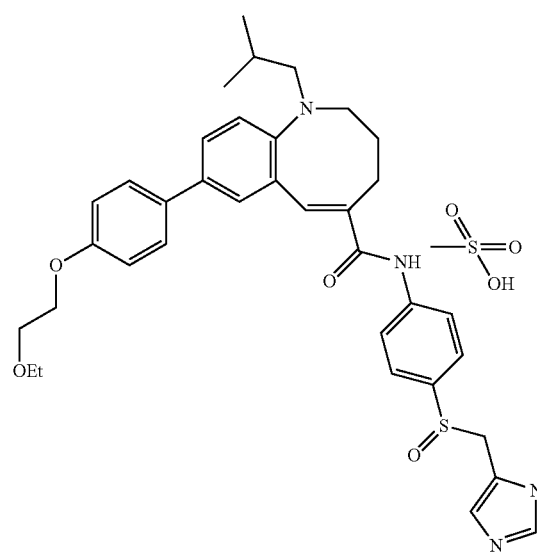
(I—MsOH—A)
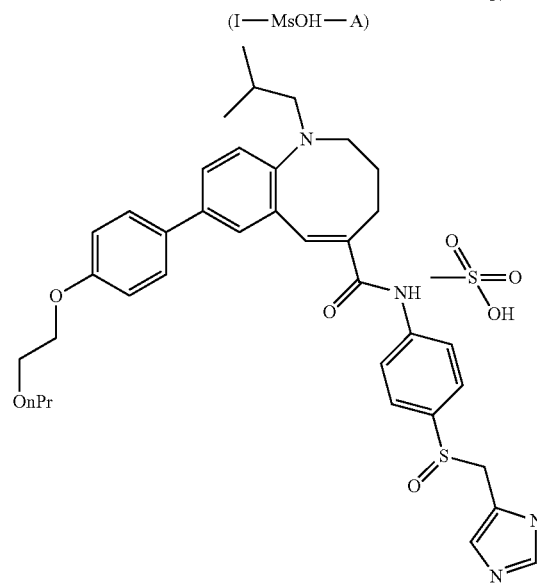
(I—MsOH—B)
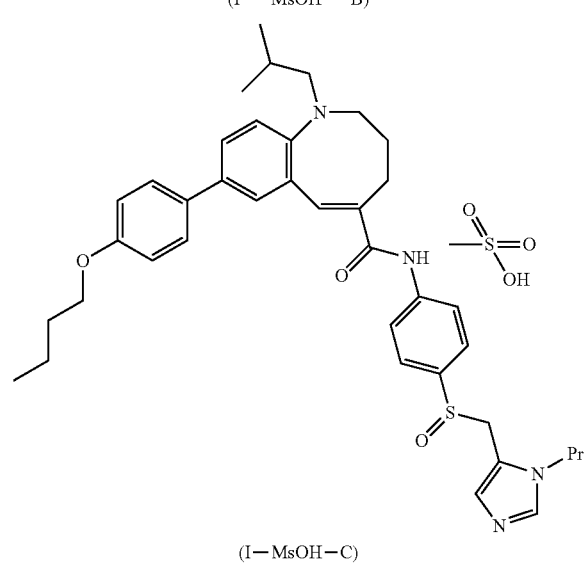
(I—MsOH—C)
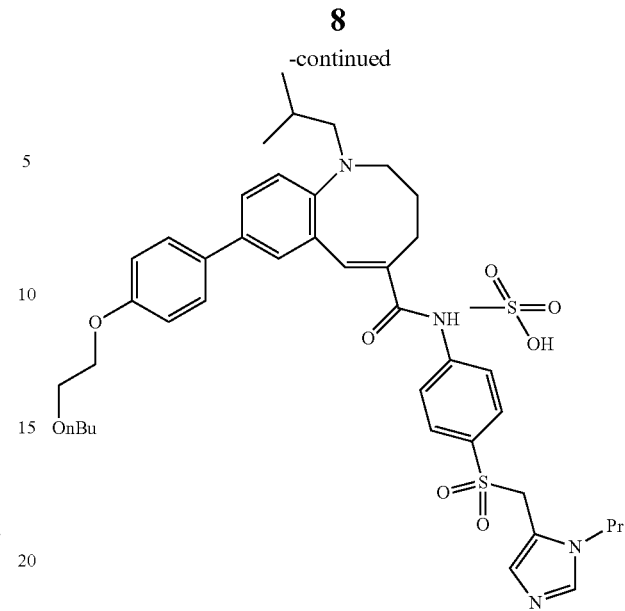
(I—MsOH—D)
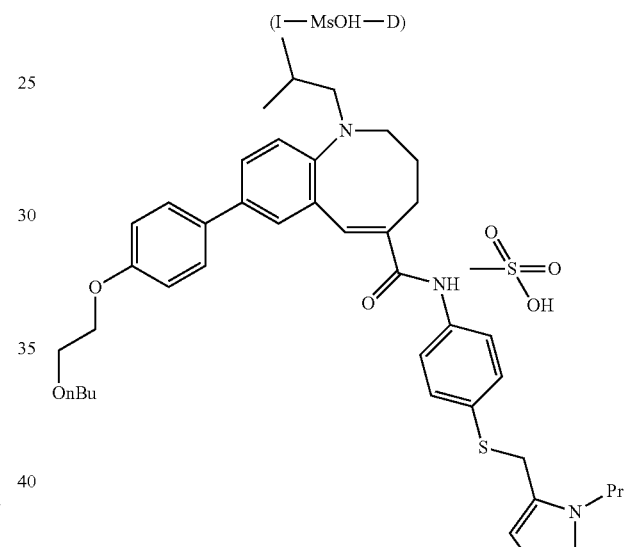
(I—MsOH—E)
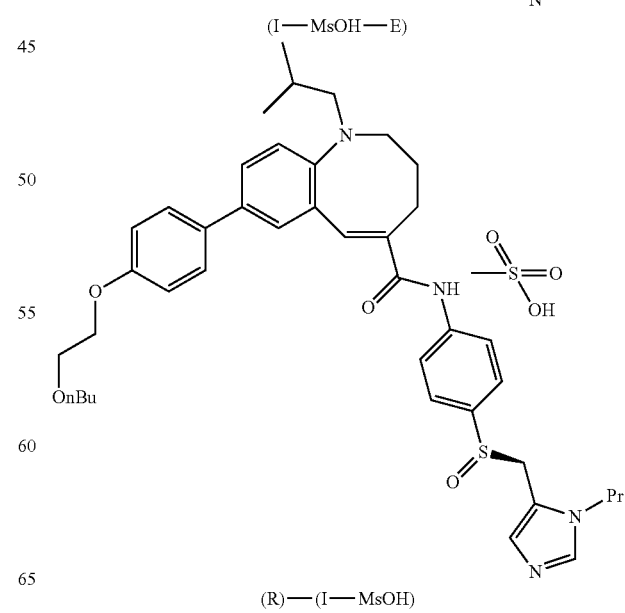
(R)—(I—MsOH)

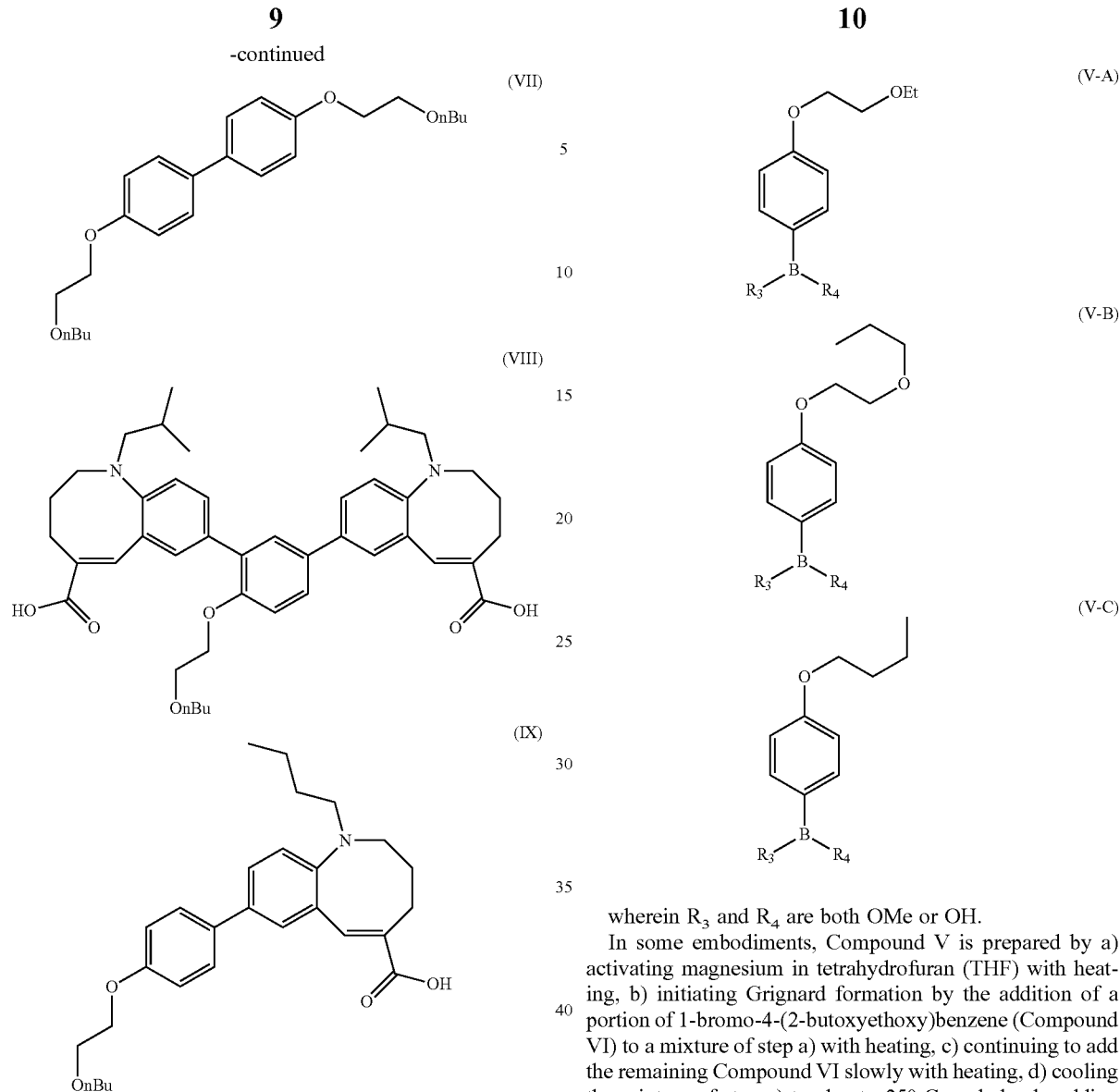

The present disclosure includes a process for preparing highly purified 8-(4-(2-butoxyethoxy)phenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH). For example, the synthesis of Compound I-MsOH includes formation of dimethyl (4-(2-butoxyethoxy)phenyl)boronate (Compound V-OMe) which is subsequently used in formation of highly pure 8-(4-(2-butoxyethoxy)phenyl)-1-isobutyl-1,2,3,4-tetrahydrobenzo[b]azocine-5-carboxylic acid (Compound II-OH).

Compound I-MsOH is prepared from (4-(2-butoxyethoxy)phenyl)boronate (Compound V-OMe) and/or (4-(2-butoxyethoxy)phenyl)boronic acid (Compound V-OH) and/or 2,4,6-tris(4-(2-butoxyethoxy)phenyl)-1,3,5,2,4,6-trioxatriborinane (Compound V-3). Compound I-MsOH is prepared from Compound V-OH and/or Compound V-3. Compound I-MsOH is prepared from Compound V-OH and/or Compound V-3 which is essentially free of Compounds V-A, V-B, and/or V-C:

wherein $R_3$ and $R_4$ are both OMe or OH.

In some embodiments, Compound V is prepared by a) activating magnesium in tetrahydrofuran (THF) with heating, b) initiating Grignard formation by the addition of a portion of 1-bromo-4-(2-butoxyethoxy)benzene (Compound VI) to a mixture of step a) with heating, c) continuing to add the remaining Compound VI slowly with heating, d) cooling the mixture of step c) to about −25° C. and slowly adding trimethoxyborane, and e) stirring the mixture of step d at about −25° C. for about 1 hour and then warming up the reaction to about 20° C. for about 1 hour.

In some embodiments, the molar ratio of Compound VI and trimethoxyborane used is about 1:1.

In some embodiments, neat Compound VI is used in steps b) and/or c). In other embodiments, step c) requires reaction to stir at about 55° C. for about 3 hours to about 5 hours.

Compound V synthesized as described herein, in one embodiment, is then utilized in the synthesis of Compound II-OH. In some embodiments, Compound II-OH is prepared by a) forming a biphasic mixture by adding a basic aqueous solution to a solution of Compound V, b) adding a catalyst and a ligand to mixture of step a), c) adding 8-bromo-1-isobutyl-1,2,3,4-tetrahydrobenzo[b]azocine-5-carboxylic acid (Compound IV) to the mixture of step b) and heating the reaction mixture, and d) acidifying the mixture of step c). The base used in step a), in some embodiments, is selected from the group consisting of potassium phosphate, potassium carbonate, potassium acetate, potassium fluoride, potassium hydroxide, potassium tert-butoxide, sodium carbonate, sodium phosphate, sodium hydroxide, sodium tert-butoxide, sodium bicarbonate, cesium carbonate, cesium fluoride, and a combination thereof. In some embodiments, the catalyst used in step b) is selected from the group consisting of palladium acetate, tetrakis(triphenylphosphine) palladium, tri(dibenzylideneacetone)dipalladium, palladium chloride, palladium acetylacetonate and a combination thereof. In some embodiments, the ligand used in step b) is selected from the group consisting of tri(o-tolyl)phosphine, triphenylphosphine, tri(t-butyl)phosphine, tricyclohexylphosphine, pyridine, bipyridine, 2,2'-bis(diphenylphosphino)-1,1'-binaphthyl and a combination thereof. In another embodiment, the catalyst system of step b) comprises palladium acetate and tri(o-tolyl)phosphine.

In some embodiments, the ratio of catalyst to ligand is about 1:2. In other embodiments, the catalyst used in step b) is in an amount from about 0.001 equivalents (equiv) to about 2.500 equiv with respect to Compound IV. In a further embodiment, the catalyst is used in an amount of about 0.001 equiv to about 0.005 equiv with respect to Compound IV. In some embodiments, nitrogen is bubbled into the reaction after step a) up to step d) or during any steps a) through d).

In some embodiments, Compound V is used in an amount of about 1.5 equiv to about 2.2 equiv with respect to Compound IV in the formation of Compound II-OH. In another embodiment, the heating of step c) is maintained at ≤65° C. for about 2 hours to about 6 hours and ensured high conversion to Compound II-OH.

In other embodiments, during purification step after step d), charcoal is added, with or without Celite® to the reaction mixture containing Compound II-OH. In another embodiment, the mixture containing charcoal and/or Celite® and Compound II-OH is stirred, and then filtered. In one embodiment, the ratio of charcoal to Celite® is about 1:2.

In another embodiment, during purification step after step d), Celite® is added to the reaction mixture containing Compound II-OH, stirred, and then filtered. In one embodiment, during the purification step after step d), the reaction mixture is filtered to remove any solid particulates.

In some embodiments, purification of Compound II-OH involves an antisolvent recrystallization and/or a hot recrystallization. In some embodiments, the antisolvent used in the antisolvent recrystallization is heptane, to obtain a crude material. In other embodiments, hot recrystallization involves the steps of i) dissolving crude material obtained from antisolvent recrystallization with a non-protic polar solvent and a short-chain alcohol at about 70° C., ii) reducing the temperature of the mixture of step i) to about 20° C. over a period of about 3 hours to about 7 hours, and iii) stirring the mixture of step ii) at about 20° C. for about 2 hours to about 6 hours. In one embodiment, the non-protic solvent is ethyl acetate. In another embodiment, the short-chain alcohol is isopropanol.

The present disclosure further describes the process for the preparation of 8-(4-(2-butoxyethoxy)phenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH). The disclosed process for synthesizing Compound I-MsOH involves a) reacting Compound II with 4-(((1-propyl-1H-imidazol-5-yl)methyl)sulfinyl)aniline (Compound III) in the presence of a base to form 8-(4-(2-butoxyethoxy)phenyl)-1-isobutyl-N-(4-(((1-propyl-1H-imidazol-5-yl)methyl)sulfinyl)phenyl)-1,2,3,4-tetrahydrobenzo[b]azocine-5-carboxamide (Compound I), b) quenching step a) with an aqueous solution, c) adding methanesulfonic acid, and d) crystallizing Compound I-MsOH. In some embodiments, $R_1$ of Compound II is selected from the group consisting of H, OH, Cl, Br, $OR_2$, $OCOR_2$, and $NHR_2$, and $R_2$ of Compound II is selected from the group consisting of H, alkyl, substituted alkyl, aryl, and substituted aryl.

In some embodiments, $R_1$ of Compound II is Cl. In one embodiment, synthesis of Compound II involves the steps of i) dissolving Compound II-OH in a solvent and ii) adding a chlorinating reagent to the mixture of step i). In some embodiments, the chlorinating reagent is selected from the group consisting of thionyl chloride, phosphorous trichloride, phosphorus pentachloride, phosphorus oxychloride, oxalyl chloride, phosgene, and a combination thereof. In one embodiment, the chlorinating reagent is thionyl chloride. In some embodiments, the chlorinating reagent is used in about 1.0 equiv to about 1.2 equiv with respect to Compound II-OH.

In some embodiments, step a) of the synthesis of Compound I-MsOH uses dichloromethane as the solvent. In other embodiments, step a) synthesis of Compound I-MsOH uses pyridine as the base. In another embodiments, step a) synthesis of Compound I-MsOH uses optically pure (S)-Compound III as Compound III.

In some embodiments, the amount of Compound III used is about 1.0 equiv to about 1.2 equiv with respect to Compound II-OH. In some embodiments, the amount of methane sulfonic acid used is about 0.97 equiv to about 1.02 equiv with respect to Compound II-OH. In other embodiments, the ratio of methane sulfonic acid and Compound II-OH is about 1:1.

In some embodiments, step b) of the synthesis of Compound I-MsOH uses citric acid as the aqueous solution. In other embodiments, step b) of the synthesis of Compound I-MsOH further comprises extracting Compound I and drying the extracted solution with 3 Å molecular sieves.

In some embodiments, pure sample of Compound I-MsOH is used to seed in the crystallization step d) of the synthesis of Compound I-MsOH. The seeded crystallization solution of step d), in some embodiments, comprise further steps of stirring at about 0° C. to allow crystallization, collecting formed crystals, and washing collected crystals with chilled ethyl acetate. In one embodiment, the formed crystals are collected by filtration.

In other embodiments, further purification is required by employing hot recrystallization after step d). The hot recrystallization of Compound I-MsOH involves i) dissolving crude crystals of Compound I-MsOH obtained in step d) in acetonitrile at about 70° C., ii) reducing the temperature of the mixture of step i) to about 50° C. to about 55° C. over about 1 hour, iii) seeding step ii) with Compound I-MsOH, iv) stirring at about 50° C. to about 55° C. for about 6 hours, v) reducing the temperature of the mixture of step iii to about 20° C., vi) stirring at about 20° C. for about 8 hours, vii) collecting crystals of Compound I-MsOH by filtration, and viii) washing crystals with cold acetonitrile.

The present disclosure describes 8-(4-(2-butoxyethoxy)phenyl)-1-isobutyl-1,2,3,4-tetrahydrobenzo[b]azocine-5-carboxylic acid (Compound II-OH), which can be characterized by its purity and by the amount of impurities. In one embodiment, Compound II-OH comprises one or more of the following: (a) about ≤0.50% to about ≥0.30% or about ≤0.01% of 8-(4-(2-ethoxyethoxy)phenyl)-1-isobutyl-1,2,3,4-tetrahydrobenzo[b]azocine-5-carboxylic acid (Compound II-OH-A); (b) about ≤0.50% to about ≥0.30% or about ≤0.01% of 1-isobutyl-8-(4-(2-propoxyethoxy)phenyl)-1,2,3,4-tetrahydrobenzo[b]azocine-5-carboxylic acid (Compound II-OH-B); (c) about ≤0.50% to about ≥0.30% of 4,4'-bis(2-butoxyethoxy)biphenyl (Compound VII); and (d) about ≤0.50% to about ≥0.30% or about ≤0.01% of 8,8'-(4-(2- butoxyethoxy)-1,3-phenylene)bis(1-isobutyl-1,2,3,4-tetrahydrobenzo[b]azocine-5-carboxylic acid) (Compound VIII); and optionally further comprises one or both of about ≤0.50% of 8-(4-butoxyphenyl)-1-isobutyl-1,2,3,4-tetrahydrobenzo[b]azocine-5-carboxylic acid (Compound II-OH-C); and about ≤0.50% of 8-(4-(2-butoxyethoxy)phenyl)-1-butyl-1,2,3,4-tetrahydrobenzo[b]azocine-5-carboxylic acid (Compound IX).

In one embodiment, Compound II-OH comprises one or both of (a) about ≤0.50% to about ≥0.30% of Compound II-OH-A; and (b) about ≤0.50% to about ≥0.30% of Compound II-OH-B; and optionally further comprises about ≤0.50% of Compound II-OH-C. In other embodiments, Compound II-OH comprises: (a) about ≤0.50% to about ≥0.30% of Compound II-OH-A; (b) about ≤0.50% to about ≥0.30% of Compound II-OH-B; and (c) about ≤0.50% of Compound II-OH-C.

In one embodiment, Compound II-OH comprises one or both of: (a) about ≤0.01% of Compound II-OH-A; and (b) about ≤0.01% of Compound II-OH-B; and optionally further comprises about ≤0.10% of Compound II-OH-C. In some embodiments, Compound II-OH comprises (a) about ≤0.01% of Compound II-OH-A; (b) about ≤0.01% of Compound II-OH-B; and (c) about ≤0.10% of Compound II-OH-C.

In one embodiment, Compound II-OH comprises one or both of: (a) about ≤0.50% to about ≥0.30% of Compound VII; and (b) about ≤0.50% to about ≥0.30% of Compound VIII; and optionally further comprises about ≤0.50% of Compound IX. In other embodiments, Compound II-OH comprises (a) about ≤0.50% to about ≥0.30% of Compound VII; (b) about ≤0.50% to about ≥0.30% of Compound VIII; and (c) about ≤0.50% of Compound IX. In some embodiments, Compound II-OH comprises about ≤0.01% of Compound VIII, and optionally further comprises one or both of (i) about ≤0.05% of Compound VII, and (ii) about ≤0.15% of Compound IX. In further embodiment, Compound II-OH comprises: (a) about ≤0.05% of Compound VII; (b) about ≤0.01% of Compound VIII; and (c) about ≤0.15% of Compound IX.

In one embodiment, Compound II-OH comprises about ≤0.50% to about ≥0.30% of Compound II-OH-A. In some embodiments, Compound II-OH comprises ≤0.01% of Compound II-OH-A.

In one embodiment, Compound II-OH comprises about ≤0.50% to about ≥0.30% of Compound II-OH-B. In some embodiments, Compound II-OH comprises ≤0.01% of Compound II-OH-B.

In one embodiment, Compound II-OH comprises about ≤0.50% to about ≥0.30% of Compound VII. In one embodiment, Compound II-OH comprises about ≤0.50% to about ≥0.30% of Compound VIII. In some embodiments, Compound II-OH comprises ≤0.01% of Compound VIII.

In some embodiments, Compound II-OH has about ≥95.0% to about ≤96.0% purity. In another embodiment, Compound II-OH has about >97.0% purity.

In some embodiments, Compound II-OH has about ≥95.0% to about ≤96.0% purity and comprises 4,4'-bis(2-butoxyethoxy)biphenyl (Compound VII) in 0.20% or less. In some embodiments, Compound II-OH has about ≥95.0% to about ≤96.0% purity and comprises 8,8'-(4-(2-butoxyethoxy)-1,3-phenylene)bis(1-isobutyl-1,2,3,4-tetrahydrobenzo[b]azocine-5-carboxylic acid) (Compound VIII) in 0.50% or less. In one embodiment, Compound II-OH has about ≥95.0% to about ≤96.0% purity and comprises 8-(4-(2-butoxyethoxy)phenyl)-1-butyl-1,2,3,4-tetrahydrobenzo[b]azocine-5-carboxylic acid (Compound IX) in 0.50% or less.

In some embodiments, Compound II-OH has about ≥95.0% to about ≤96.0% purity and comprises 4,4'-bis(2-butoxyethoxy)biphenyl (Compound VII) t in 0.10% or less; or 8,8'-(4-(2-butoxyethoxy)-1,3-phenylene)bis(1-isobutyl-1,2,3,4-tetrahydrobenzo[b]azocine-5-carboxylic acid) (Compound VIII) in 0.10% or less; or 8-(4-(2-butoxyethoxy)phenyl)-1-butyl-1,2,3,4-tetrahydrobenzo[b]azocine-5-carboxylic acid (Compound IX) in 0.15% or less. In other embodiments, Compound II-OH has about ≥95.0% to about ≤96.0% purity and comprises one or more of the following: (a) 0.50% or less of 8-(4-(2-ethoxyethoxy)phenyl)-1-isobutyl-1,2,3,4-tetrahydrobenzo[b]azocine-5-carboxylic acid (Compound II-OH-A); (b) 0.50% or less of 1-isobutyl-8-(4-(2-propoxyethoxy)phenyl)-1,2,3,4-tetrahydrobenzo[b]azocine-5-carboxylic acid (Compound II-OH-B); (c) 0.50% or less of 8-(4-butoxyphenyl)-1-isobutyl-1,2,3,4-tetrahydrobenzo[b]azocine-5-carboxylic acid (Compound II-OH-C); (d) 0.50% or less of 8,8'-(4-(2-butoxyethoxy)-1,3-phenylene)bis(1-isobutyl-1,2,3,4-tetrahydrobenzo[b]azocine-5-carboxylic acid) (Compound VIII); and/or (e) 0.50% or less of 8-(4-(2-butoxyethoxy)phenyl)-1-butyl-1,2,3,4-tetrahydrobenzo[b]azocine-5-carboxylic acid (Compound IX).

In one embodiment, Compound II-OH has about ≥95.0% to about ≤96.0% purity and comprises Compound II-OH-A in 0.10% or less. In other embodiments, Compound II-OH has about ≥95.0% to about ≤96.0% purity and comprises Compound II-OH-C in 0.10% or less. In some embodiments, Compound II-OH has about ≥95.0% to about ≤96.0% purity and comprises Compound VIII in 0.10% or less. In a further embodiment, Compound II-OH has about ≥95.0% to about ≤96.0% purity and comprises Compound IX in 0.20% or less.

In other embodiments, Compound II-OH has about ≥95.0% to about ≤96.0% purity and comprises one or more of the following: (a) 0.05% or less of 8-(4-(2-ethoxyethoxy)phenyl)-1-isobutyl-1,2,3,4-tetrahydrobenzo[b]azocine-5-carboxylic acid (Compound II-OH-A); (b) 0.05% or less of 1-isobutyl-8-(4-(2-propoxyethoxy)phenyl)-1,2,3,4-tetrahydrobenzo[b]azocine-5-carboxylic acid (Compound II-OH-B); (c) 0.05% or less of 8-(4-butoxyphenyl)-1-isobutyl-1,2,3,4-tetrahydrobenzo[b]azocine-5-carboxylic acid (Compound II-OH-C); (d) 0.05% or less of 8,8'-(4-(2-butoxyethoxy)-1,3-phenylene)bis(1-isobutyl-1,2,3,4-tetrahydrobenzo[b]azocine-5-carboxylic acid) (Compound VIII); and/or (e) 0.15% or less of 8-(4-(2-butoxyethoxy)phenyl)-1-butyl-1,2,3,4-tetrahydrobenzo[b]azocine-5-carboxylic acid (Compound IX).

The present disclosure describes 8-(4-(2-butoxyethoxy)phenyl)-1-isobutyl-N-(4-(2-(1-propyl-1H-imidazol-5-yl)acetyl)phenyl)-1,2,3,4-tetrahydrobenzo[b]azocine-5-carboxamide methanesulfonate (Compound I-MsOH), which can be characterized by its purity and by the amount of impurities. In one embodiment, Compound I-MsOH, or an enantiomer, a stereoisomer, or a combination thereof, with a purity of ≥96.0% or ≥98.5% or higher, wherein said compound comprises one or more of the following: (a) about ≤0.50% to about ≥0.30% of 8, 8'-(4-(2-butoxyethoxy)-1,3-phenylene)bis(1-isobutyl-1,2,3,4-tetrahydrobenzo[b]azocine-5-carboxylic acid) (Compound VIII); (b) about ≤0.50% to about ≥0.30% of 8-(4-(2-butoxyethoxy)phenyl)-1-butyl-1,2,3,4-tetrahydrobenzo[b]azocine-5-carboxylic acid (Compound IX); (c) about ≤0.50% to about ≥0.30% of 8-(4-(2-ethoxyethoxy)phenyl)-1-isobutyl-N-(4-(((1-propyl-1H-imidazol-5-yl)methyl)sulfinyl)phenyl)-1,2,3,4- tetrahydrobenzo[b]azocine-5-carboxamide methanesulfonate (Compound I-MsOH-A); (d) about ≤0.50% to about ≥0.30% of 1-isobutyl-8-(4-(2-propoxyethoxy)phenyl)-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-B); (e) about ≤0.50% to about ≥0.45% of 8-(4-butoxyphenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-C); (f) about ≤0.50% to about ≥0.45% of 8-(4-(2-butoxyethoxy)phenyl)-1-isobutyl-N-(4-(((1-propyl-1H-imidazol-5-yl)methyl)thio)phenyl)-1,2,3,4-tetrahydrobenzo[b]azocine-5-carboxamide methanesulfonate (Compound I-MsOH-E); (g) about ≤0.50% to about ≥0.45% of 8-(4-(2-butoxyethoxy)phenyl)-1-butyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-F); and (h) about ≤0.50% to about ≥0.45% of 8,8'-(4-(2-butoxyethoxy)-1,3-phenylene)bis(1-isobutyl-N-(4-(((1-propyl-1H-imidazol-5-yl)methyl)sulfinyl)phenyl)-1,2,3,4-tetrahydrobenzo[b]azocine-5-carboxamide) dimethanesulfonate (Compound I-MsOH-G).

In one embodiment, Compound I-MsOH, or an enantiomer, a stereoisomer, or a combination thereof, with a purity of ≥96.0% or ≥98.5% or higher comprises ≤1.0% of 8-(4-(2-butoxyethoxy)phenyl)-1-isobutyl-1,2,3,4-tetrahydrobenzo[b]azocine-5-carboxylic acid (Compound II-OH). In another embodiment, Compound I-MsOH, or an enantiomer, a stereoisomer, or a combination thereof, with a purity of ≥96.0% or ≥98.5% or higher comprises 2000 ppm or less of 4-(((1-propyl-1H-imidazol-5-yl)methyl)sulfinyl)aniline (Compound III). In some embodiments, Compound III is present in 1500 ppm or less.

In one embodiment, Compound I-MsOH, or an enantiomer, a stereoisomer, or a combination thereof, with a purity of ≥96.0% or ≥98.5% or higher comprises ≤2.0% of 8-(4-(2-butoxyethoxy)phenyl)-1-isobutyl-N-(4-(((1-propyl-1H-imidazol-5-yl)methyl)sulfonyl)phenyl)-1,2,3,4-tetrahydrobenzo[b]azocine-5-carboxamide methanesulfonate (Compound I-MsOH-D). In some embodiment, Compound I-MsOH-D is present in ≤1.0%.

In one embodiment, Compound I-MsOH, or an enantiomer, a stereoisomer, or a combination thereof, with a purity of ≥96.0% or ≥98.5% or higher comprises ≤0.10% of 8,8'-(4-(2-butoxyethoxy)-1,3-phenylene)bis(1-isobutyl-1,2,3,4-tetrahydrobenzo[b]azocine-5-carboxylic acid) (Compound VIII), provided that there is present one or more of: (b) about ≤0.50% to about ≥0.30% of Compound IX; (c) about ≤0.50% to about ≥0.30% of Compound I-MsOH-A; (d) about ≤0.50% to about ≥0.30% of Compound I-MsOH-B; (e) about ≤0.50% to about ≥0.45% of Compound I-MsOH-C; (f) about ≤0.50% to about ≥0.45% of Compound I-MsOH-E; (g) about ≤0.50% to about ≥0.45% of Compound I-MsOH-F; and (h) about ≤0.50% to about ≥0.45% of Compound I-MsOH-G.

In one embodiment, Compound I-MsOH, or an enantiomer, a stereoisomer, or a combination thereof, with a purity of ≥96.0% or ≥98.5% or higher comprises ≤0.10% of 8-(4-(2-butoxyethoxy)phenyl)-1-butyl-1,2,3,4-tetrahydrobenzo[b]azocine-5-carboxylic acid (Compound IX), provided that there is present one or more of: (a) about ≤0.50% to about ≥0.30% of Compound VIII; (c) about ≤0.50% to about ≥0.30% of Compound I-MsOH-A; (d) about ≤0.50% to about ≥0.30% of Compound I-MsOH-B; (e) about ≤0.50% to about ≥0.45% of Compound I-MsOH-C; (f) about ≤0.50% to about ≥0.45% of Compound I-MsOH-E; (g) about ≤0.50% to about ≥0.45% of Compound I-MsOH-F; and (h) about ≤0.50% to about ≥0.45% of Compound I-MsOH-G.

In one embodiment, Compound I-MsOH, or an enantiomer, a stereoisomer, or a combination thereof, with a purity of ≥96.0% or ≥98.5% or higher comprises ≤0.10% of 8-(4-(2-butoxyethoxy)phenyl)-1-butyl-1,2,3,4-tetrahydrobenzo[b]azocine-5-carboxylic acid (Compound IX), provided that there is present one or more of: (a) about ≤0.50% to about ≥0.30% of Compound VIII; (b) about ≤0.50% to about ≥0.30% of Compound IX; (d) about ≤0.50% to about ≥0.30% of Compound I-MsOH-B; (e) about ≤0.50% to about ≥0.45% of Compound I-MsOH-C; (f) about ≤0.50% to about ≥0.45% of Compound I-MsOH-E; (g) about ≤0.50% to about ≥0.45% of Compound I-MsOH-F; and (h) about ≤0.50% to about ≥0.45% of Compound I-MsOH-G.

In one embodiment, Compound I-MsOH, or an enantiomer, a stereoisomer, or a combination thereof, with a purity of ≥96.0% or ≥98.5% or higher comprises ≤0.15% of 1-isobutyl-8-(4-(2-propoxyethyl)phenyl)-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-B), provided that there is present one or more of: (a) about ≤0.50% to about ≥0.30% of Compound VIII; (b) about ≤0.50% to about ≥0.30% of Compound IX; (d) about ≤0.50% to about ≥0.30% of Compound I-MsOH-B; (c) about ≤0.50% to about ≥0.30% of Compound I-MsOH-A; (e) about ≤0.50% to about ≥0.45% of Compound I-MsOH-C; (f) about ≤0.50% to about ≥0.45% of Compound I-MsOH-E; (g) about ≤0.50% to about ≥0.45% of Compound I-MsOH-F; and (h) about ≤0.50% to about ≥0.45% of Compound I-MsOH-G.

In one embodiment, Compound I-MsOH, or an enantiomer, a stereoisomer, or a combination thereof, with a purity of ≥96.0% or ≥98.5% or higher comprises ≤0.30% of 8-(4-butoxyphenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-C), provided that there is present one or more of: (a) about ≤0.50% to about ≥0.30% of Compound VIII; (b) about ≤0.50% to about ≥0.30% of Compound IX; (d) about ≤0.50% to about ≥0.30% of Compound I-MsOH-B; (c) about ≤0.50% to about ≥0.30% of Compound I-MsOH-A; (d) about ≤0.50% to about ≥0.30% of Compound I-MsOH-B; (f) about ≤0.50% to about ≥0.45% of Compound I-MsOH-E; (g) about ≤0.50% to about ≥0.45% of Compound I-MsOH-F; and (h) about ≤0.50% to about ≥0.45% of Compound I-MsOH-G.

In one embodiment, Compound I-MsOH, or an enantiomer, a stereoisomer, or a combination thereof, with a purity of ≥96.0% or ≥98.5% or higher comprises ≤0.30% of 8-(4-(2-butoxyethoxy)phenyl)-1-iso butyl-N-(4-(((1-propyl-1H-imidazol-5-yl)methyl)thio)phenyl)-1,2,3,4-tetrahydrobenzo[b]azocine-5-carboxamide methanesulfonate (Compound I-MsOH-E), provided that there is present one or more of: (a) about ≤0.50% to about ≥0.30% of Compound VIII; (b) about ≤0.50% to about ≥0.30% of Compound IX; (d) about ≤0.50% to about ≥0.30% of Compound I-MsOH-B; (c) about ≤0.50% to about ≥0.30% of Compound I-MsOH-A; (d) about ≤0.50% to about ≥0.30% of Compound I-MsOH-B; (e) about ≤0.50% to about ≥0.45% of Compound I-MsOH-C; (g) about ≤0.50% to about ≥0.45% of Compound I-MsOH-F; and (h) about ≤0.50% to about ≥0.45% of Compound I-MsOH-G.

In one embodiment, Compound I-MsOH, or an enantiomer, a stereoisomer, or a combination thereof, with a purity of ≥96.0% or ≥98.5% or higher comprises ≤0.20% of 8-(4-(2-butoxyethoxy)phenyl)-1-butyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-F), provided that there is present one or more of: (a) about ≤0.50% to about ≥0.30% of Compound VIII; (b) about ≤0.50% to about ≥0.30% of Compound IX; (d) about ≤0.50% to about ≥0.30% of Compound I-MsOH-B; (c) about ≤0.50% to about ≥0.30% of Compound I-MsOH-A; (d) about ≤0.50% to about ≥0.30% of Compound I-MsOH-B; (e) about ≤0.50% to about ≥0.45% of Compound I-MsOH-C; (f) about ≤0.50% to about ≥0.45% of Compound I-MsOH-E; and (h) about ≤0.50% to about ≥0.45% of Compound I-MsOH-G.

In one embodiment, Compound I-MsOH, or an enantiomer, a stereoisomer, or a combination thereof, with a purity of ≥96.0% or ≥98.5% or higher comprises ≤0.15% of 8,8'-(4-(2-butoxyethoxy)-1,3-phenylene)bis(1-isobutyl-N-(4-(((1-propyl-1H-imidazol-5-yl)methyl)sulfinyl)phenyl)-1,2,3,4-tetrahydrobenzo[b]azocine-5-carboxamide) dimethanesulfonate (Compound I-MsOH-G), provided that there is present one or more of: (a) about ≤0.50% to about ≥0.30% of Compound VIII; (b) about ≤0.50% to about ≥0.30% of Compound IX; (d) about ≤0.50% to about ≥0.30% of Compound I-MsOH-B; (c) about ≤0.50% to about ≥0.30% of Compound I-MsOH-A; (d) about ≤0.50% to about ≥0.30% of Compound I-MsOH-B; (e) about ≤0.50% to about ≥0.45% of Compound I-MsOH-C; (f) about ≤0.50% to about ≥0.45% of Compound I-MsOH-E; and (g) about ≤0.50% to about ≥0.45% of Compound I-MsOH-F.

In one embodiment, Compound I-MsOH, or an enantiomer, a stereoisomer, or a combination thereof, with a purity of ≥96.0% or ≥98.5% or higher comprises one or more of the following: (i) ≤0.30% of 8-(4-(2-butoxyethoxy)phenyl)-1-isobutyl-1,2,3,4-tetrahydrobenzo[b]azocine-5-carboxylic acid (Compound II-OH); (ii) ≤0.05% of 8,8'-(4-(2-butoxyethoxy)-1,3-phenylene)bis(1-isobutyl-1,2,3,4-tetrahydrobenzo[b]azocine-5-carboxylic acid) (Compound VIII); and (iii) ≤0.05% of 8-(4-(2-butoxyethoxy)phenyl)-1-butyl-1,2,3,4-tetrahydrobenzo[b]azocine-5-carboxylic acid (Compound IX), provided there is present one or more of compounds: (c) about ≤0.50% to about ≥0.30% of Compound I-MsOH-A; (d) about ≤0.50% to about ≥0.30% of Compound I-MsOH-B; (e) about ≤0.50% to about ≥0.45% of Compound I-MsOH-C; (f) about ≤0.50% to about ≥0.45% of Compound I-MsOH-E; (g) about ≤0.50% to about ≥0.45% of Compound I-MsOH-F; and (h) about ≤0.50% to about ≥0.45% of Compound I-MsOH-G.

In one embodiment, Compound I-MsOH, or an enantiomer, a stereoisomer, or a combination thereof, with a purity of ≥96.0% or ≥98.5% or higher comprises one or more of the following: (i) 1300 ppm or less wherein 4-(((1-propyl-1H-imidazol-5-yl)methyl)sulfinyl)aniline (Compound III); (ii) ≤0.10% of 8-(4-(2-ethoxyethoxy)phenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-A); (iii) ≤0.10% of 1-isobutyl-8-(4-(2-propoxyethoxy)phenyl)-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-B); (iv) ≤0.20% of 8-(4-butoxyphenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-C); (v) ≤0.80% of 8-(4-(2-butoxyethoxy)phenyl)-1-isobutyl-N-(4-(((1-propyl-1H-imidazol-5-yl)methyl)sulfonyl)phenyl)-1,2,3,4-tetrahydrobenzo[b]azocine-5-carboxamide methanesulfonate (Compound I-MsOH-D); (vi) ≤0.20% of 8-(4-(2-butoxyethoxy)phenyl)-1-isobutyl-N-(4-(((1-propyl-1H-imidazol-5-yl)methyl)thio)phenyl)-1,2,3,4-tetrahydrobenzo[b]azocine-5-carboxamide methanesulfonate (Compound I-MsOH-E); (vii) ≤0.15% of 8-(4-(2-butoxyethoxy)phenyl)-1-butyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-F); and (viii) ≤0.10% of 8,8'-(4-(2-butoxyethoxy)-1,3-phenylene)bis(1-isobutyl-N-(4-(((1-propyl-1H-imidazol-5-yl)methyl)sulfinyl)phenyl)-1,2,3,4-tetrahydrobenzo[b]azocine-5-carboxamide) dimethanesulfonate (Compound I-MsOH-G), provided there is present one or more of compounds (a) about ≤0.50% to about ≥0.30% of Compound VIII and (b) about ≤0.50% to about ≥0.30% of Compound IX.

In one embodiment, Compound I-MsOH, or an enantiomer, a stereoisomer, or a combination thereof, with a purity of ≥96.0% or ≥98.5% or higher comprising mesylate ester resulting from MsOH in 0.001% or less, or 10 ppm or less.

In one embodiment, Compound I-MsOH as disclosed herein is (S)-8-(4-(2-butoxyethoxy)phenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate ((S)-Compound I-MsOH). In some embodiments, (S)-Compound I-MsOH comprises ≤0.5% of (R)-8-(4-(2-butoxyethoxy)phenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate ((R)-Compound I-MsOH). In some embodiments, (S)-Compound I-MsOH comprises ≤0.2% of (R)-Compound I-MsOH.

In some embodiments, (S)-Compound I-MsOH comprises 5.0% w/w or less or 2.0% w/w or less water content.

DETAILED DESCRIPTION OF THE DISCLOSURE

Definitions

Figure 1:
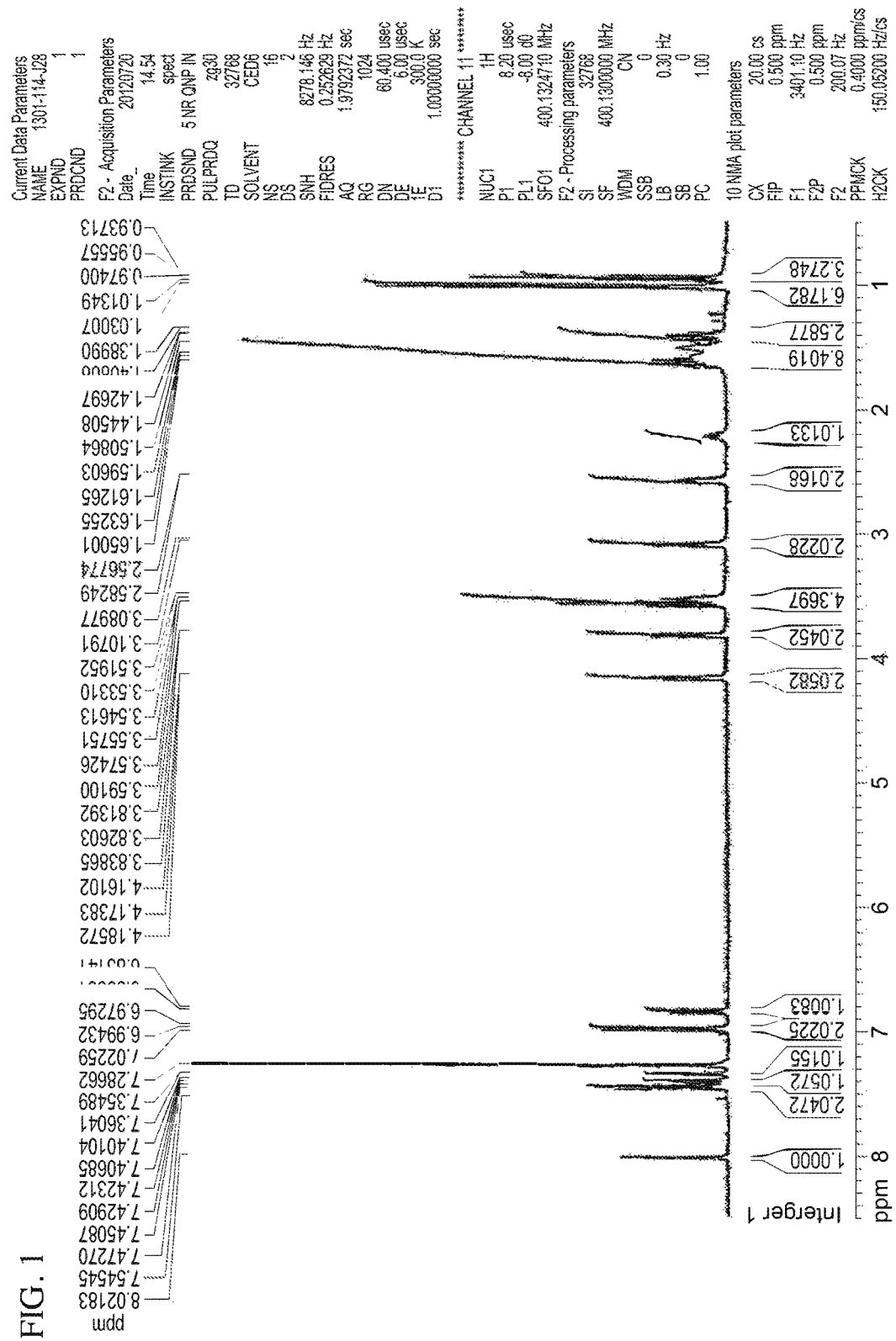
FIG. 1. shows a proton NMR (nuclear magnetic resonance spectroscopy) spectrum of (S)-Compound II-OH.

While the following terms are believed to be well understood by one of ordinary skill in the art, the following definitions are set forth to facilitate explanation of the presently disclosed subject matter.

The term "a" or "an" refers to one or more of that entity; for example, "a halogen" refers to one or more halogens or at least one halogen. As such, the terms "a" (or "an"), "one or more" and "at least one" are used interchangeably herein. In addition, reference to "an alkyl group" by the indefinite article "a" or "an" does not exclude the possibility that more than one of the alkyl group is present, unless the context clearly requires that there is one and only one of the alkyl groups.

As used herein, the verb "comprise" as is used in this description and in the claims and its conjugations are used in its non-limiting sense to mean that items following the word are included, but items not specifically mentioned are not excluded.

As used herein, the phrase "alkyl group" refers to a straight chain, a branched chain or a cyclic hydrocarbons having from 1 up to about 10 carbon atoms. Non-limiting examples of an alkyl group includes C1-C10 alkyl group such as methyl, ethyl, propyl, isopropyl, butyl, isobutyl, sec-butyl, tert-butyl, pentyl, isopentyl, neopentyl, hexyl, heptyl, octyl, nonyl, decyl, and the like.

As used herein the phrase "aryl group" refers to an aromatic group having from 6 up to 14 carbon atoms. Non-limiting examples of an aryl group includes phenyl, naphthyl, anthryl, fluorenyl, and the like.

As used herein, the phrase "substituent(s)" in the optionally substituted alkyl group and the optionally substituted aryl group includes a halogen atom (e.g., fluorine, chlorine, bromine, iodine, etc.), a nitro group, a cyano group, an optionally substituted hydroxyl group (e.g., a hydroxyl group, C1-C4 alkoxy, etc.), an optionally substituted thiol group (e.g., thiol, C1-C4 alkylthio, etc.), an optionally substituted amino group (e.g., amino, mono-C1-C4 alkylamino, di-C1-C4 alkylamino, a 5- or 6-membered cyclic amino group such as, pyrrolidine, piperazine, piperidine, morpholine, thiomorpholine, pyrrole and imidazole, etc.), an optionally esterified or amidated carboxyl group (e.g., carboxyl, C1-C4 alkoxycarbonyl, carbamoyl, mono-C1-C4 alkylcarbamoyl, di-C1-C4 alkylcarbamoyl, etc.), an optionally halogenated C1-C4 alkoxy group (e.g., methoxy, ethoxy, propoxy, butoxy, trifluoromethoxy, trifluoroethoxy, etc.), an optionally halogenated C1-C4 alkoxy-C1-C4 alkoxy group (e.g., methoxymethoxy, methoxyethoxy, ethoxyethoxy, trifluoromethoxyethoxy, trifluoroethoxyethoxy, etc.), a formyl group, a C2-C4 alkanoyl group (e.g., acetyl, propionyl, etc.) and a C1-C4 alkylsulfonyl group (e.g., methanesulfonyl, ethanesulfonyl, etc.).

As used herein, the phrase "short-chain alcohol" refers to alcohol containing 1-8 carbon atoms. Non-limiting examples of short-chain alcohol includes methanol, ethanol, propanol, isopropanol, butanol, pentanol, hexanol, heptanol, octanol, and the like.

As used herein, the phrase "nonprotic solvent" or "non-protic solvent" refers to an organic solvent or mixtures of organic solvents that is not readily deprotonated in the presence of a strongly basic reactant. Non-limiting examples of non-protic solvents include ethers, dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide, diethoxymethane, tetrahydrofuran, 1,3-dioxane, 1,4-dioxane, furan, diethyl ether, tetrahydropyran, diisopropyl ether, dibutyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, and the like.

As used herein, the phrase "protic solvent" refers to a solvent or solvent mixtures that is capable of functioning as an acid for purposes of protonating any unreacted, strongly basic reaction intermediates. Non-limiting examples of protic solvents include water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol, and the like.

As used herein, the phrase "part(s)" when used to describe volume of a liquid refers to an approximate estimate of the volume multiplier to a compound, substance, or liquid in which it refers to or which is stated previously. For example, 50 parts water with respect to Compound A means water with approximately 50 times the volume of Compound A is used.

As used herein, the symbol "≤" means "not more than" or "equal to or less than"; "<" means "less than"; "≥" means "not less than" or "equal to or more than"; and ">" means "more than". Furthermore, the numerical numbers, when used herein in connection with purity or impurity content, include not only the exact number but also the approximate range around the number. For example, the phrase "purity of 99.0%" denotes a purity of about 99.0%.

Compounds and Purities/Impurities

The compounds of the disclosure, or their pharmaceutically acceptable salts can contain one or more asymmetric centers and can thus give rise to enantiomers, diastereomers, and other stereoisomeric forms that can be defined, in terms of absolute stereochemistry, as (R)- or (S)-. The present disclosure is meant to include all such possible isomers, as well as their racemic and optically pure forms whether or not they are specifically depicted herein. Optically active (+) and (−), or (R)- and (S)-isomers can be prepared using chiral synthons or chiral reagents, or resolved using conventional techniques, for example, chromatography and fractional crystallization.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another. In one embodiment, compounds disclosed herein include racemic mixtures, enantiomers, diastereomers, or enantiomerically or diastereomerically enriched mixtures.

The disclosed process, in some embodiments, for the synthesis of Compound II-OH provides Compound II-OH in about ≥95.0% to about ≤96.0% purity. In another embodiment, the disclosed process for the synthesis of Compound II-OH provides Compound II-OH in about >97.0% purity. In one embodiment, the disclosed process for the synthesis of Compound II-OH provides Compound II-OH in about >97.5% purity. In another embodiment, the disclosed process for the synthesis of Compound II-OH provides Compound II-OH in about >98.0% purity. In some embodiments, the disclosed process for the synthesis of Compound II-OH provides Compound II-OH in about >99.0% purity.

In other embodiments, the disclosed synthesis of Compound II-OH results in the presence of 4,4'-bis(2-butoxyethoxy)biphenyl (Compound VII) in about ≤0.50% to about ≥0.30%. In one embodiment, the disclosed synthesis of Compound II-OH results in the presence of Compound VII in about ≤0.20%. In one embodiment, the disclosed synthesis of Compound II-OH results in the presence of Compound VII in about ≤0.10%. In some embodiment, the disclosed synthesis of Compound II-OH results in the presence of Compound VII in about ≤0.05%.

In other embodiments, the disclosed synthesis of Compound II-OH results in the presence of 8,8'-(4-(2-butoxyethoxy)-1,3-phenylene)bis(1-isobutyl-1,2,3,4-tetrahydrobenzo[b]azocine-5-carboxylic acid) (Compound VIII) in about ≤0.50% to about >0.20%. In other embodiments, the disclosed synthesis of Compound II-OH results in the presence of 8,8'-(4-(2-butoxyethoxy)-1,3-phenylene)bis(1-isobutyl-1,2,3,4-tetrahydrobenzo[b]azocine-5-carboxylic acid) (Compound VIII) in about ≤0.50% to about ≥0.25%. In other embodiments, the disclosed synthesis of Compound II-OH results in the presence of 8,8'-(4-(2-butoxyethoxy)-1,3-phenylene)bis(1-isobutyl-1,2,3,4-tetrahydrobenzo[b]azocine-5-carboxylic acid) (Compound VIII) in about ≤0.50% to about ≥0.30%. In one embodiment, the disclosed synthesis of Compound II-OH results in the presence of 8,8'-(4-(2-butoxyethoxy)-1,3-phenylene)bis(1-isobutyl-1,2,3,4-tetrahydrobenzo[b]azocine-5-carboxylic acid) (Compound VIII) in about ≤0.20%. In other embodiments, the disclosed synthesis of Compound II-OH results in the presence of 8,8'-(4-(2-butoxyethoxy)-1,3-phenylene)bis(1-isobutyl-1,2,3,4-tetrahydrobenzo[b]azocine-5-carboxylic acid) (Compound VIII) in about ≤0.10%. In one embodiment, the disclosed synthesis of Compound II-OH results in the presence of 8,8'-(4-(2-butoxyethoxy)-1,3-phenylene)bis(1-isobutyl-1,2,3,4-tetrahydrobenzo[b]azocine-5-carboxylic acid) (Compound VIII) in about ≤0.05%. In some embodiments, the disclosed synthesis of Compound II-OH results in the presence of 8,8'-(4-(2-butoxyethoxy)-1,3-phenylene)bis(1-isobutyl-1,2,3,4-tetrahydrobenzo[b]azocine-5-carboxylic acid) (Compound VIII) in about ≤0.01%.

In other embodiments, the disclosed synthesis of Compound II-OH results in the presence of 8-(4-(2-butoxyethoxy)phenyl)-1-butyl-1,2,3,4-tetrahydrobenzo[b]azocine-5-carboxylic acid (Compound IX) in about ≤0.50%. In another embodiment, the disclosed synthesis of Compound II-OH results in the presence of 8-(4-(2-butoxyethoxy)phenyl)-1-butyl-1,2,3,4-tetrahydrobenzo[b]azocine-5-carboxylic acid (Compound IX) in about ≤0.25%. In one embodiment, the disclosed synthesis of Compound II-OH results in the presence of 8-(4-(2-butoxyethoxy)phenyl)-1-butyl-1,2,3,4-tetrahydrobenzo[b]azocine-5-carboxylic acid (Compound IX) in about ≤0.15%. In one embodiment, the disclosed synthesis of Compound II-OH results in the presence of Compound IX in about ≤0.10%. In one embodiment, the disclosed synthesis of Compound II-OH results in the presence of Compound IX in about ≤0.05%.

In some embodiments, the disclosed synthesis of Compound II-OH result in the presence of 8-(4-(2-ethoxyethoxy)phenyl)-1-isobutyl-1,2,3,4-tetrahydrobenzo[b]azocine-5-carboxylic acid (Compound II-OH-A) in about ≤0.50% to about ≥0.20%. In some embodiments, the disclosed synthesis of Compound II-OH result in the presence of 8-(4-(2-ethoxyethoxy)phenyl)-1-isobutyl-1,2,3,4-tetrahydrobenzo[b]azocine-5-carboxylic acid (Compound II-OH-A) in about ≤0.50% to about ≥0.25%. In some embodiments, the disclosed synthesis of Compound II-OH result in the presence of 8-(4-(2-ethoxyethoxy)phenyl)-1-isobutyl-1,2,3,4-tetrahydrobenzo[b]azocine-5-carboxylic acid (Compound II-OH-A) in about ≤0.50% to about ≥0.30%. In one embodiment, the disclosed synthesis of Compound II-OH results in the presence of 8-(4-(2-ethoxyethoxy)phenyl)-1-isobutyl-1,2,3,4-tetrahydrobenzo[b]azocine-5-carboxylic acid (Compound II-OH-A) in about ≤0.20%. In other embodiments, the disclosed synthesis of Compound II-OH results in the presence of 8-(4-(2-ethoxyethoxy)phenyl)-1-isobutyl-1,2,3,4-tetrahydrobenzo[b]azocine-5-carboxylic acid (Compound II-OH-A) in about ≤0.10%. In one embodiment, the disclosed synthesis of Compound II-OH results in the presence of 8-(4-(2-ethoxyethoxy)phenyl)-1-isobutyl-1,2,3,4-tetrahydrobenzo[b]azocine-5-carboxylic acid (Compound II-OH-A) in about ≤0.05%. In another embodiment, the disclosed synthesis of Compound II-OH results in the presence of 8-(4-(2-ethoxyethoxy)phenyl)-1-isobutyl-1,2,3,4-tetrahydrobenzo[b]azocine-5-carboxylic acid (Compound II-OH-A) in about ≤0.01%.

In some embodiments, the disclosed synthesis of Compound II-OH results in the presence of 1-isobutyl-8-(4-(2-propoxyethoxy)phenyl)-1,2,3,4-tetrahydrobenzo[b]azocine-5-carboxylic acid (Compound II-OH-B) in about ≤0.50% to about ≥0.20%. In some embodiments, the disclosed synthesis of Compound II-OH results in the presence of 1-isobutyl-8-(4-(2-propoxyethoxy)phenyl)-1,2,3,4-tetrahydrobenzo[b]azocine-5-carboxylic acid (Compound II-OH-B) in about ≤0.50% to about ≥0.25%. In some embodiments, the disclosed synthesis of Compound II-OH results in the presence of 1-isobutyl-8-(4-(2-propoxyethoxy)phenyl)-1,2,3,4-tetrahydrobenzo[b]azocine-5-carboxylic acid (Compound II-OH-B) in about ≤0.50% to about ≥0.30%. In one embodiment, the disclosed synthesis of Compound II-OH results in the presence of 1-isobutyl-8-(4-(2-propoxyethoxy)phenyl)-1,2,3,4-tetrahydrobenzo[b]azocine-5-carboxylic acid (Compound II-OH-B) in about ≤0.20%. In one embodiment, the disclosed synthesis of Compound II-OH results in the presence of 1-isobutyl-8-(4-(2-propoxyethoxy)phenyl)-1,2,3,4-tetrahydrobenzo[b]azocine-5-carboxylic acid (Compound II-OH-B) in about ≤0.10%. In one embodiment, the disclosed synthesis of Compound II-OH results in the presence of 1-isobutyl-8-(4-(2-propoxyethoxy)phenyl)-1,2,3,4-tetrahydrobenzo[b]azocine-5-carboxylic acid (Compound II-OH-B) in about ≤0.05%. In another embodiment, the disclosed synthesis of Compound II-OH results in the presence of 1-isobutyl-8-(4-(2-propoxyethoxy)phenyl)-1,2,3,4-tetrahydrobenzo[b]azocine-5-carboxylic acid (Compound II-OH-B) in about ≤0.01%.

In one embodiment, the disclosed synthesis of Compound II-OH results in the presence of 8-(4-butoxyphenyl)-1-isobutyl-1,2,3,4-tetrahydrobenzo[b]azocine-5-carboxylic acid (Compound II-OH-C) in about ≤0.50%. In some embodiments, the disclosed synthesis of Compound II-OH results in the presence of 8-(4-butoxyphenyl)-1-isobutyl-1,2,3,4-tetrahydrobenzo[b]azocine-5-carboxylic acid (Compound II-OH-C) in about ≤0.25%. In one embodiment, the disclosed synthesis of Compound II-OH results in the presence of 8-(4-butoxyphenyl)-1-isobutyl-1,2,3,4-tetrahydrobenzo[b]azocine-5-carboxylic acid (Compound II-OH-C) in about ≤0.15%. In other embodiments, the disclosed synthesis of Compound II-OH results in the presence of 8-(4-butoxyphenyl)-1-isobutyl-1,2,3,4-tetrahydrobenzo[b]azocine-5-carboxylic acid (Compound II-OH-C) in about ≤0.10%. In other embodiments, the disclosed synthesis of Compound II-OH results in the presence of Compound II-OH-C in about ≤0.05%. In other embodiments, the disclosed synthesis of Compound II-OH results in the presence of Compound II-OH-C in about ≤0.01%.

In one embodiment, the disclosed synthesis of Compound II-OH results in the presence of one or more of the following:

(a) about ≤0.50% to about ≥0.30% or about ≤0.01% of 8-(4-(2-ethoxyethoxy)phenyl)-1-isobutyl-1,2,3,4-tetrahydrobenzo[b]azocine-5-carboxylic acid (Compound II-OH-A);

(b) about ≤0.50% to about ≥0.30% or about ≤0.01% of 1-isobutyl-8-(4-(2-propoxyethoxy)phenyl)-1,2,3,4-tetrahydrobenzo[b]azocine-5-carboxylic acid (Compound II-OH-B);

(c) about ≤0.50% to about ≥0.30% of 4,4'-bis(2-butoxyethoxy)biphenyl (Compound VII); and (d) about ≤0.50% to about ≥0.30% or about ≤0.01% of 8,8'-(4-(2-butoxyethoxy)-1,3-phenylene)bis(1-isobutyl-1,2, 3,4-tetrahydrobenzo[b]azocine-5-carboxylic acid) (Compound VIII); and optionally further comprises one or both of
(i) about ≤0.50% of 8-(4-butoxyphenyl)-1-isobutyl-1,2,3,4-tetrahydrobenzo[b]azocine-5-carboxylic acid (Compound II-OH-C); and
(ii) about ≤0.50% of 8-(4-(2-butoxyethoxy)phenyl)-1-butyl-1,2,3,4-tetrahydrobenzo[b]azocine-5-carboxylic acid (Compound IX).

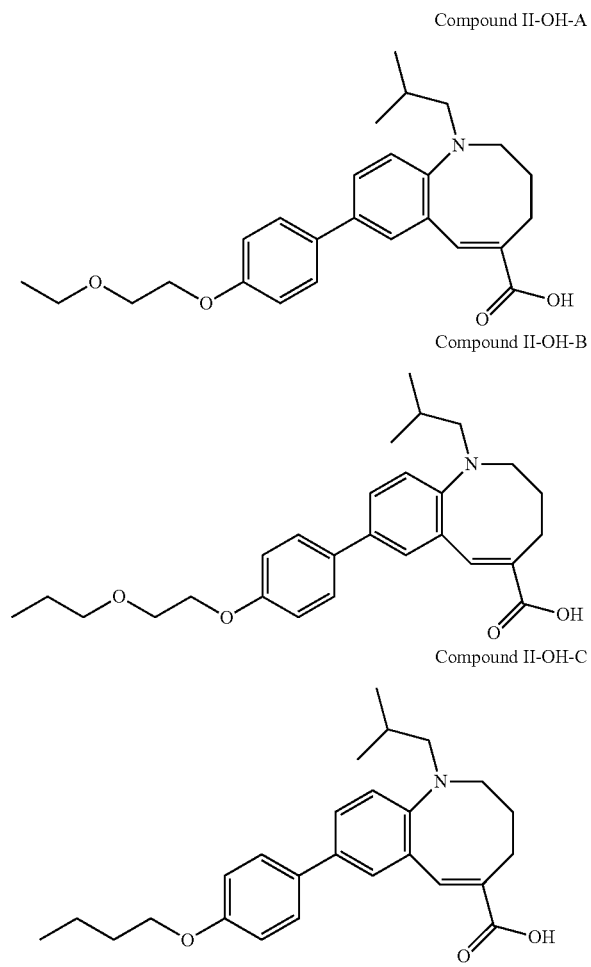

Compound II-OH-A

Compound II-OH-B

Compound II-OH-C

The disclosed process, in some embodiments, the synthesis of Compound I-MsOH provides Compound I-MsOH or an enantiomer, a stereoisomer, or a combination thereof, in about ≥95.0% to about ≤95.5% purity. In one embodiment, the disclosed process for the synthesis of Compound I-MsOH provides Compound I-MsOH or an enantiomer, a stereoisomer, or a combination thereof, in about ≥96.0% purity. In another embodiment, the disclosed process for the synthesis of Compound I-MsOH provides Compound I-MsOH or an enantiomer, a stereoisomer, or a combination thereof, in about ≥97.0% purity. In one embodiment, the disclosed process for the synthesis of Compound I-MsOH provides Compound I-MsOH or an enantiomer, a stereoisomer, or a combination thereof, in about >98.0% purity. In some embodiments, the disclosed process for the synthesis of Compound I-MsOH provides Compound I-MsOH or an enantiomer, a stereoisomer, or a combination thereof, in about ≥98.5% purity.

In other embodiments, the disclosed synthesis of Compound I-MsOH or an enantiomer, a stereoisomer, or a combination thereof, results in the presence of 8-(4-(2-butoxyethoxy)phenyl)-1-isobutyl-1,2,3,4-tetrahydrobenzo[b]azocine-5-carboxylic acid (Compound II-OH) in about ≤1.0%. In one embodiment, the disclosed synthesis of Compound I-MsOH or an enantiomer, a stereoisomer, or a combination thereof, results in the presence of 8-(4-(2-butoxyethoxy)phenyl)-1-isobutyl-1,2,3,4-tetrahydrobenzo[b]azocine-5-carboxylic acid (Compound II-OH) in about ≤0.80% or about ≤0.50%. In some embodiments, the disclosed synthesis of Compound I-MsOH or an enantiomer, a stereoisomer, or a combination thereof, results in the presence of 8-(4-(2-butoxyethoxy)phenyl)-1-isobutyl-1,2,3,4-tetrahydrobenzo[b]azocine-5-carboxylic acid (Compound II-OH) in about ≤0.25%.

In other embodiments, the disclosed synthesis of Compound I-MsOH or an enantiomer, a stereoisomer, or a combination thereof, results in the presence of 8,8'-(4-(2-butoxyethoxy)-1,3-phenylene)bis(1-isobutyl-1,2,3,4-tetrahydrobenzo[b]azocine-5-carboxylic acid) (Compound VIII) in about ≤0.50% to about ≥0.20%. In other embodiments, the disclosed synthesis of Compound I-MsOH or an enantiomer, a stereoisomer, or a combination thereof, results in the presence of 8,8'-(4-(2-butoxyethoxy)-1,3-phenylene)bis(1-isobutyl-1,2,3,4-tetrahydrobenzo[b]azocine-5-carboxylic acid) (Compound VIII) in about ≤0.50% to about ≥0.25%. In other embodiments, the disclosed synthesis of Compound I-MsOH or an enantiomer, a stereoisomer, or a combination thereof, results in the presence of 8,8'-(4-(2-butoxyethoxy)-1,3-phenylene)bis(1-isobutyl-1,2,3,4-tetrahydrobenzo[b]azocine-5-carboxylic acid) (Compound VIII) in about ≤0.50% to about ≥0.30%. In some embodiments, the disclosed synthesis of Compound I-MsOH or an enantiomer, a stereoisomer, or a combination thereof, results in the presence of 8,8'-(4-(2-butoxyethoxy)-1,3-phenylene)bis(1-isobutyl-1,2,3,4-tetrahydrobenzo[b]azocine-5-carboxylic acid) (Compound VIII) in about ≤0.20%. In one embodiment, the disclosed synthesis of Compound I-MsOH or an enantiomer, a stereoisomer, or a combination thereof, results in the presence of 8,8'-(4-(2-butoxyethoxy)-1,3-phenylene)bis(1-isobutyl-1,2,3,4-tetrahydrobenzo[b]azocine-5-carboxylic acid) (Compound VIII) in about ≤0.10%. In one embodiment, the disclosed synthesis of Compound I-MsOH or an enantiomer, a stereoisomer, or a combination thereof, results in the presence of 8,8'-(4-(2-butoxyethoxy)-1,3-phenylene)bis(1-isobutyl-1,2,3,4-tetrahydrobenzo[b]azocine-5-carboxylic acid) (Compound VIII) in about ≤0.05%. In another embodiment, the disclosed synthesis of Compound I-MsOH or an enantiomer, a stereoisomer, or a combination thereof, results in the presence of 8,8'-(4-(2-butoxyethoxy)-1,3-phenylene)bis(1-isobutyl-1,2,3,4-tetrahydrobenzo[b]azocine-5-carboxylic acid) (Compound VIII) in about ≤0.01%.

In other embodiments, the disclosed synthesis of Compound I-MsOH or an enantiomer, a stereoisomer, or a combination thereof, results in the presence of 8-(4-(2-butoxyethoxy)phenyl)-1-butyl-1,2,3,4-tetrahydrobenzo[b]azocine-5-carboxylic acid (Compound IX) in about ≤0.50% to about ≥0.20%. In other embodiments, the disclosed synthesis of Compound I-MsOH or an enantiomer, a stereoisomer, or a combination thereof, results in the presence of 8-(4-(2-butoxyethoxy)phenyl)-1-butyl-1,2,3,4-tetrahydrobenzo[b]azocine-5-carboxylic acid (Compound IX) in about ≤0.50% to about ≥0.25%. In other embodiments, the disclosed synthesis of Compound I-MsOH or an enantiomer, a stereoisomer, or a combination thereof, results in the presence of 8-(4-(2-butoxyethoxy)phenyl)-1-butyl-1,2,3,4-tetrahydrobenzo[b]azocine-5-carboxylic acid (Compound IX) in about ≤0.50% to about ≥0.30%. In one embodiment, the disclosed synthesis of Compound I-MsOH or an enantiomer, a stereoisomer, or a combination thereof, results in the presence of 8-(4-(2-butoxyethoxy)phenyl)-1-butyl-1,2,3,4-tetrahydrobenzo[b]azocine-5-carboxylic acid (Compound IX) in about ≤0.25%. In one embodiment, the disclosed synthesis of Compound I-MsOH or an enantiomer, a stereoisomer, or a combination thereof, results in the presence of 8-(4-(2-butoxyethoxy)phenyl)-1-butyl-1,2,3,4-tetrahydrobenzo[b]azocine-5-carboxylic acid (Compound IX) in about ≤0.20%. In one embodiment, the disclosed synthesis of Compound I-MsOH or an enantiomer, a stereoisomer, or a combination thereof, results in the presence of 8-(4-(2-butoxyethoxy)phenyl)-1-butyl-1,2,3,4-tetrahydrobenzo[b]azocine-5-carboxylic acid (Compound IX) in about ≤0.15%. In one embodiment, the disclosed synthesis of Compound I-MsOH or an enantiomer, a stereoisomer, or a combination thereof, results in the presence of 8-(4-(2-butoxyethoxy)phenyl)-1-butyl-1,2,3,4-tetrahydrobenzo[b]azocine-5-carboxylic acid (Compound IX) in about ≤0.10%. In some embodiments, the disclosed synthesis of Compound I-MsOH or an enantiomer, a stereoisomer, or a combination thereof, results in the presence of 8-(4-(2-butoxyethoxy)phenyl)-1-butyl-1,2,3,4-tetrahydrobenzo[b]azocine-5-carboxylic acid (Compound IX) in about ≤0.05%.

In some embodiments, the disclosed synthesis of Compound I-MsOH or an enantiomer, a stereoisomer, or a combination thereof, results in the presence of 4-(((1-propyl-1H-imidazol-5-yl)methyl)sulfinyl)aniline (Compound III) or an enantiomer, a stereoisomer, or a combination thereof, in about ≤0.50% to about ≥0.35%. In one embodiment, the disclosed synthesis of Compound I-MsOH or an enantiomer, a stereoisomer, or a combination thereof, results in the presence of 4-(((1-propyl-1H-imidazol-5-yl)methyl)sulfinyl)aniline (Compound III) or an enantiomer, a stereoisomer, or a combination thereof, in about ≤0.25%. In one embodiment, the disclosed synthesis of Compound I-MsOH or an enantiomer, a stereoisomer, or a combination thereof, results in the presence of 4-(((1-propyl-1H-imidazol-5-yl)methyl)sulfinyl)aniline (Compound III) or an enantiomer, a stereoisomer, or a combination thereof, in about ≤0.15%. In another embodiment, the disclosed synthesis of Compound I-MsOH or an enantiomer, a stereoisomer, or a combination thereof, results in the presence of 4-(((1-propyl-1H-imidazol-5-yl)methyl)sulfinyl)aniline (Compound III) or an enantiomer, a stereoisomer, or a combination thereof, in about ≤0.10%.

In some embodiments, the disclosed synthesis of Compound I-MsOH or an enantiomer, a stereoisomer, or a combination thereof, results in the presence of 4-(((1-propyl-1H-imidazol-5-yl)methyl)sulfinyl)aniline (Compound III) or an enantiomer, a stereoisomer, or a combination thereof, in about ≤2000 ppm. In some embodiments, the disclosed synthesis of Compound I-MsOH or an enantiomer, a stereoisomer, or a combination thereof, results in the presence of 4-(((1-propyl-1H-imidazol-5-yl)methyl)sulfinyl)aniline (Compound III) or an enantiomer, a stereoisomer, or a combination thereof, in about ≤1750 ppm. In some embodiments, the disclosed synthesis of Compound I-MsOH or an enantiomer, a stereoisomer, or a combination thereof, results in the presence of 4-(((1-propyl-1H-imidazol-5-yl)methyl)sulfinyl)aniline (Compound III) or an enantiomer, a stereoisomer, or a combination thereof, in about ≤1500 ppm. In some embodiments, the disclosed synthesis of Compound I-MsOH or an enantiomer, a stereoisomer, or a combination thereof, results in the presence of 4-(((1-propyl-1H-imidazol-5-yl)methyl)sulfinyl)aniline (Compound III) or an enantiomer, a stereoisomer, or a combination thereof, in about ≤1250 ppm.

In one embodiment, the disclosed synthesis of Compound I-MsOH or an enantiomer, a stereoisomer, or a combination thereof, results in the presence of (S)-4-(((1-propyl-1H-imidazol-5-yl)methyl)sulfinyl)aniline ((S)-Compound III) in about ≤1500 ppm.

In some embodiments, the disclosed synthesis of Compound I-MsOH or an enantiomer, a stereoisomer, or a combination thereof, results in the presence of 8-(4-(2-ethoxyethoxy)phenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-A) in about ≤0.50% to about >0.25%. In some embodiments, the disclosed synthesis of Compound I-MsOH or an enantiomer, a stereoisomer, or a combination thereof, results in the presence of 8-(4-(2-ethoxyethoxy)phenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-A) in about ≤0.50% to about ≥0.30%. In one embodiment, the disclosed synthesis of Compound I-MsOH or an enantiomer, a stereoisomer, or a combination thereof, results in the presence of 8-(4-(2-ethoxyethoxy)phenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-A) in about ≤0.25%. In one embodiment, the disclosed synthesis of Compound I-MsOH or an enantiomer, a stereoisomer, or a combination thereof, results in the presence of 8-(4-(2-ethoxyethoxy)phenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-A) in about ≤0.15%. In another embodiment, the disclosed synthesis of Compound I-MsOH or an enantiomer, a stereoisomer, or a combination thereof, results in the presence of 8-(4-(2-ethoxyethoxy)phenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-A) in about ≤0.10%.

In some embodiments, the disclosed synthesis of Compound I-MsOH or an enantiomer, a stereoisomer, or a combination thereof, results in the presence of 1-isobutyl-8-(4-(2-propoxyethoxy)phenyl)-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-B) in about ≤0.50% to about ≥0.25%. In some embodiments, the disclosed synthesis of Compound I-MsOH or an enantiomer, a stereoisomer, or a combination thereof, results in the presence of 1-isobutyl-8-(4-(2-propoxyethoxy)phenyl)-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-B) in about ≤0.50% to about ≥0.30%. In one embodiment, the disclosed synthesis of Compound I-MsOH or an enantiomer, a stereoisomer, or a combination thereof, results in the presence of 1-isobutyl-8-(4-(2-propoxyethoxy)phenyl)-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-B) in about ≤0.25%. In other embodiments, the disclosed synthesis of Compound I-MsOH or an enantiomer, a stereoisomer, or a combination thereof, results in the presence of 1-isobutyl-8-(4-(2-propoxyethoxy)phenyl)-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-B) in about ≤0.15%. In one embodiment, the disclosed synthesis of Compound I-MsOH or an enantiomer, a stereoisomer, or a combination thereof, results in the presence of 1-isobutyl-8-(4-(2-propoxyethoxy)phenyl)-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-B) in about ≤0.10%.

In some embodiments, the disclosed synthesis of Compound I-MsOH or an enantiomer, a stereoisomer, or a combination thereof, results in the presence of 8-(4-butoxyphenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-C) in about ≤0.50% to about >0.40%. In some embodiments, the disclosed synthesis of Compound I-MsOH or an enantiomer, a stereoisomer, or a combination thereof, results in the presence of 8-(4-butoxyphenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-C) in about ≤0.50% to about ≥0.45%. In one embodiment, the disclosed synthesis of Compound I-MsOH or an enantiomer, a stereoisomer, or a combination thereof, results in the presence of 8-(4-butoxyphenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-C) in about ≤0.40%. In other embodiments, the disclosed synthesis of Compound I-MsOH or an enantiomer, a stereoisomer, or a combination thereof, results in the presence of 8-(4-butoxyphenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-C) in about ≤0.30%. In one embodiment, the disclosed synthesis of Compound I-MsOH or an enantiomer, a stereoisomer, or a combination thereof, results in the presence of 8-(4-butoxyphenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-C) in about ≤0.20%. In another embodiment, the disclosed synthesis of Compound I-MsOH or an enantiomer, a stereoisomer, or a combination thereof, results in the presence of 8-(4-butoxyphenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-C) in about ≤0.10%.

In one embodiment, the disclosed synthesis of Compound I-MsOH or an enantiomer, a stereoisomer, or a combination thereof, results in the presence of 8-(4-(2-butoxyethoxy)phenyl)-1-isobutyl-N-(4-(((1-propyl-1H-imidazol-5-yl)methyl)sulfonyl)phenyl)-1,2,3,4-tetrahydrobenzo[b]azocine-5-carboxamide methanesulfonate (Compound I-MsOH-D) in about ≤2.0%. In other embodiments, the disclosed synthesis of Compound I-MsOH or an enantiomer, a stereoisomer, or a combination thereof, results in the presence of 8-(4-(2-butoxyethoxy)phenyl)-1-isobutyl-N-(4-(((1-propyl-1H-imidazol-5-yl)methyl)sulfonyl)phenyl)-1,2,3,4-tetrahydrobenzo[b]azocine-5-carboxamide methanesulfonate (Compound I-MsOH-D) in about ≤1.0%. In one embodiment, the disclosed synthesis of Compound I-MsOH or an enantiomer, a stereoisomer, or a combination thereof, results in the presence of 8-(4-(2-butoxyethoxy)phenyl)-1-isobutyl-N-(4-(((1-propyl-1H-imidazol-5-yl)methyl)sulfonyl)phenyl)-1,2,3,4-tetrahydrobenzo[b]azocine-5-carboxamide methanesulfonate (Compound I-MsOH-D) in about ≤0.50%. In another embodiment, the disclosed synthesis of Compound I-MsOH or an enantiomer, a stereoisomer, or a combination thereof, results in the presence of 8-(4-(2-butoxyethoxy)phenyl)-1-isobutyl-N-(4-(((1-propyl-1H-imidazol-5-yl)methyl)sulfonyl)phenyl)-1,2,3,4-tetrahydrobenzo[b]azocine-5-carboxamide methanesulfonate (Compound I-MsOH-D) in about ≤0.10%.

In some embodiments, the disclosed synthesis of Compound I-MsOH or an enantiomer, a stereoisomer, or a combination thereof, results in the presence of 8-(4-(2-butoxyethoxy)phenyl)-1-isobutyl-N-(4-(((1-propyl-1H-imidazol-5-yl)methyl)thio)phenyl)-1,2,3,4-tetrahydrobenzo[b]azocine-5-carboxamide methanesulfonate (Compound I-MsOH-E) in about ≤0.50% to about >0.40%. In some embodiments, the disclosed synthesis of Compound I-MsOH or an enantiomer, a stereoisomer, or a combination thereof, results in the presence of 8-(4-(2-butoxyethoxy)phenyl)-1-isobutyl-N-(4-(((1-propyl-1H-imidazol-5-yl)methyl)thio)phenyl)-1,2,3,4-tetrahydrobenzo[b]azocine-5-carboxamide methanesulfonate (Compound I-MsOH-E) in about ≤0.50% to about ≥0.45%. In one embodiment, the disclosed synthesis of Compound I-MsOH or an enantiomer, a stereoisomer, or a combination thereof, results in the presence of 8-(4-(2-butoxyethoxy)phenyl)-1-isobutyl-N-(4-(((1-propyl-1H-imidazol-5-yl)methyl)thio)phenyl)-1,2,3,4-tetrahydrobenzo[b]azocine-5-carboxamide methanesulfonate (Compound I-MsOH-E) in about ≤0.40%. In other embodiments, the disclosed synthesis of Compound I-MsOH or an enantiomer, a stereoisomer, or a combination thereof, results in the presence of 8-(4-(2-butoxyethoxy)phenyl)-1-isobutyl-N-(4-(((1-propyl-1H-imidazol-5-yl)methyl)thio)phenyl)-1,2,3,4-tetrahydrobenzo[b]azocine-5-carboxamide methanesulfonate (Compound I-MsOH-E) in about ≤0.30%. In one embodiment, the disclosed synthesis of Compound I-MsOH or an enantiomer, a stereoisomer, or a combination thereof, results in the presence of 8-(4-(2-butoxyethoxy)phenyl)-1-isobutyl-N-(4-(((1-propyl-1H-imidazol-5-yl)methyl)thio)phenyl)-1,2,3,4-tetrahydrobenzo[b]azocine-5-carboxamide methanesulfonate (Compound I-MsOH-E) in about ≤0.20%. In another embodiment, the disclosed synthesis of Compound I-MsOH or an enantiomer, a stereoisomer, or a combination thereof, results in the presence of 8-(4-(2-butoxyethoxy)phenyl)-1-isobutyl-N-(4-(((1-propyl-1H-imidazol-5-yl)methyl)thio)phenyl)-1,2,3,4-tetrahydrobenzo[b]azocine-5-carboxamide methanesulfonate (Compound I-MsOH-E) in about ≤0.10%.

In some embodiments, the disclosed synthesis of Compound I-MsOH or an enantiomer, a stereoisomer, or a combination thereof, results in the presence of 8-(4-(2-butoxyethoxy)phenyl)-1-butyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-F) in about ≤0.50% to about >0.40%. In some embodiments, the disclosed synthesis of Compound I-MsOH or an enantiomer, a stereoisomer, or a combination thereof, results in the presence of 8-(4-(2-butoxyethoxy)phenyl)-1-butyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-F) in about ≤0.50% to about ≥0.45%. In one embodiment, the disclosed synthesis of Compound I-MsOH or an enantiomer, a stereoisomer, or a combination thereof, results in the presence of 8-(4-(2-butoxyethoxy)phenyl)-1-butyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-F) in about ≤0.40%. In other embodiments, the disclosed synthesis of Compound I-MsOH or an enantiomer, a stereoisomer, or a combination thereof, results in the presence of 8-(4-(2-butoxyethoxy)phenyl)-1-butyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-F) in about ≤0.30%. In one embodiment, the disclosed synthesis of Compound I-MsOH or an enantiomer, a stereoisomer, or a combination thereof, results in the presence of 8-(4-(2-butoxyethoxy)phenyl)-1-butyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-F) in about ≤0.20%. In one embodiment, the disclosed synthesis of Compound I-MsOH or an enantiomer, a stereoisomer, or a combination thereof, results in the presence of 8-(4-(2-butoxyethoxy)phenyl)-1-butyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-F) in about ≤0.15%. In one embodiment, the disclosed synthesis of Compound I-MsOH or an enantiomer, a stereoisomer, or a combination thereof, results in the presence of 8-(4-(2-butoxyethoxy)phenyl)-1-butyl-N-(4-(((1-propyl-1H-imidazol-5-yl)methyl)sulfinyl)phenyl)-1,2,3,4-tetrahydrobenzo[b]azocine-5-carboxamide methanesulfonate (Compound I-MsOH-F) in about ≤0.10%.

In some embodiments, the disclosed synthesis of Compound I-MsOH or an enantiomer, a stereoisomer, or a combination thereof, results in the presence of 8,8'-(4-(2-butoxyethoxy)-1,3-phenylene)bis(1-isobutyl-N-(4-(((1-propyl-1H-imidazol-5-yl)methyl)sulfinyl)phenyl)-1,2,3,4-tetrahydrobenzo[b]azocine-5-carboxamide) dimethanesulfonate (Compound I-MsOH-G) in about ≤0.50% to about >0.40%. In some embodiments, the disclosed synthesis of Compound I-MsOH or an enantiomer, a stereoisomer, or a combination thereof, results in the presence of 8,8'-(4-(2-butoxyethoxy)-1,3-phenylene)bis(1-isobutyl-N-(4-(((1-propyl-1H-imidazol-5-yl)methyl)sulfinyl)phenyl)-1,2,3,4-tetrahydrobenzo[b]azocine-5-carboxamide) dimethanesulfonate (Compound I-MsOH-G) in about ≤0.50% to about ≥0.45%. In some embodiments, the disclosed synthesis of Compound I-MsOH or an enantiomer, a stereoisomer, or a combination thereof, results in the presence of 8,8'-(4-(2-butoxyethoxy)-1,3-phenylene)bis(1-isobutyl-N-(4-(((1-propyl-1H-imidazol-5-yl)methyl)sulfinyl)phenyl)-1,2,3,4-tetrahydrobenzo[b]azocine-5-carboxamide) dimethanesulfonate (Compound I-MsOH-G) in about ≤0.50% to about ≥0.30%. In one embodiment, the disclosed synthesis of Compound I-MsOH or an enantiomer, a stereoisomer, or a combination thereof, results in the presence of 8,8'-(4-(2-butoxyethoxy)-1,3-phenylene)bis(1-isobutyl-N-(4-(((1-propyl-1H-imidazol-5-yl)methyl)sulfinyl)phenyl)-1,2,3,4-tetrahydrobenzo[b]azocine-5-carboxamide) dimethanesulfonate (Compound I-MsOH-G) in about ≤0.40%. In one embodiment, the disclosed synthesis of Compound I-MsOH or an enantiomer, a stereoisomer, or a combination thereof, results in the presence of 8,8'-(4-(2-butoxyethoxy)-1,3-phenylene)bis(1-isobutyl-N-(4-(((1-propyl-1H-imidazol-5-yl)methyl)sulfinyl)phenyl)-1,2,3,4-tetrahydrobenzo[b]azocine-5-carboxamide) dimethanesulfonate (Compound I-MsOH-G) in about ≤0.30%. In one embodiment, the disclosed synthesis of Compound I-MsOH or an enantiomer, a stereoisomer, or a combination thereof, results in the presence of 8,8'-(4-(2-butoxyethoxy)-1,3-phenylene)bis(1-isobutyl-N-(4-(((1-propyl-1H-imidazol-5-yl)methyl)sulfinyl)phenyl)-1,2,3,4-tetrahydrobenzo[b]azocine-5-carboxamide) dimethanesulfonate (Compound I-MsOH-G) in about ≤0.20%. In one embodiment, the disclosed synthesis of Compound I-MsOH or an enantiomer, a stereoisomer, or a combination thereof, results in the presence of 8,8'-(4-(2-butoxyethoxy)-1,3-phenylene)bis(1-isobutyl-N-(4-(((1-propyl-1H-imidazol-5-yl)methyl)sulfinyl)phenyl)-1,2,3,4-tetrahydrobenzo[b]azocine-5-carboxamide) dimethanesulfonate (Compound I-MsOH-G) in about ≤0.15%. The disclosed synthesis of Compound I-MsOH or an enantiomer, a stereoisomer, or a combination thereof, results in the presence of 8,8'-(4-(2-butoxyethoxy)-1,3-phenylene)bis(1-isobutyl-N-(4-(((1-propyl-1H-imidazol-5-yl)methyl)sulfinyl)phenyl)-1,2,3,4-tetrahydrobenzo[b]azocine-5-carboxamide) dimethanesulfonate (Compound I-MsOH-G) in about ≤0.10%.

In another embodiment, the disclosed synthesis of Compound I-MsOH or an enantiomer, a stereoisomer, or combinations thereof, results in the presence of mesylate esters, resulting from MsOH, in about ≤1.0%. In other embodiments, the disclosed synthesis of Compound I-MsOH results in the presence of mesylate esters, resulting from MsOH, in about ≤0.50%. In one embodiment, the disclosed synthesis of Compound I-MsOH or an enantiomer, a stereoisomer, or combinations thereof, results in the presence of mesylate esters, resulting from MsOH, in about ≤0.25%.

In one embodiment, the disclosed synthesis of Compound I-MsOH or an enantiomer, a stereoisomer, or combinations thereof, results in the presence of mesylate esters, resulting from MsOH, in about ≤20 ppm. In other embodiments, the disclosed synthesis of Compound I-MsOH results in the presence of mesylate esters, resulting from MsOH, in about ≤10 ppm. In one embodiment, the disclosed synthesis of Compound I-MsOH or an enantiomer, a stereoisomer, or combinations thereof, results in the presence of mesylate esters, resulting from MsOH, in about ≤5 ppm. In some embodiments, Compound I-MsOH or an enantiomer, a stereoisomer, or a combination thereof contains 10 ppm mesylate ester for a 150 mg dose.

I-MsOH-F

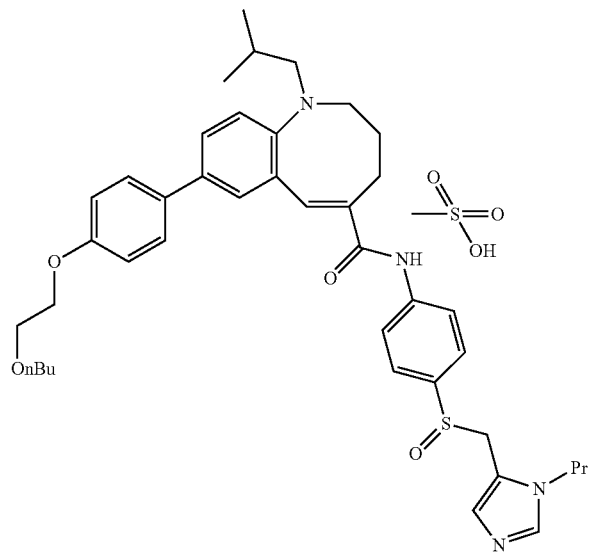

I-MsOH-G

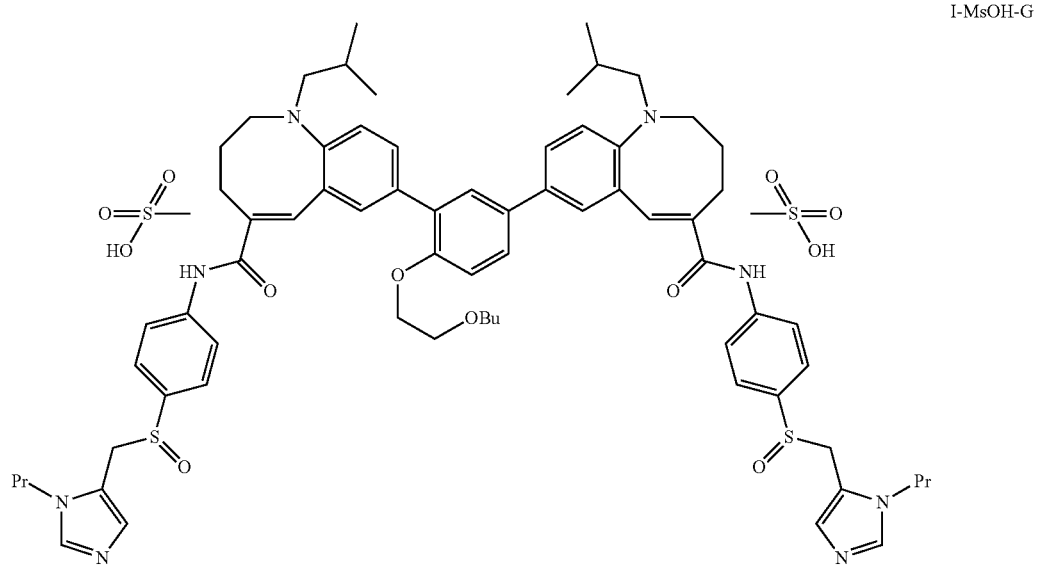

In one embodiment, the disclosed synthesis of Compound I-MsOH results in (S)-Compound I-MsOH. In some embodiments, the disclosed synthesis provides (S)-Compound I-MsOH in greater than 96% purity or greater than 98.5% purity.

In some embodiments, the disclosed synthesis of (S)-Compound I-MsOH results in the presence of (R)-8-(4-(2-butoxyethoxy)phenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate ((R)-Compound I-MsOH) in about ≤1.00%. In another embodiment, the disclosed synthesis of (S)-Compound I-MsOH results in the presence of (R)-8-(4-(2-butoxyethoxy)phenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate ((R)-Compound I-MsOH) in about ≤0.50%. In one embodiment, the disclosed synthesis of (S)-Compound I-MsOH results in the presence of (R)-8-(4-(2-butoxyethoxy)phenyl)-1-isobutyl-N-(4-(((1-propyl-1H-imidazol-5-yl)methyl)sulfinyl)phenyl)-1,2,3,4-tetrahydrobenzo[b]azocine-5-carboxamide methanesulfonate ((R)-Compound I-MsOH) in about ≤0.25%.

In some embodiments, the disclosed synthesis of Compound I-MsOH or an enantiomer, a stereoisomer, or a combination thereof, results in the presence of 5.0% w/w or less or 2.0% w/w or less water content.

In some embodiments, the disclosed synthesis of (S)-Compound I-MsOH results in the presence of ≤3.0% impurity including (R)-Compound I-MsOH but excluding (S)-Compound III. In one embodiment, the disclosed synthesis of (S)-Compound I-MsOH results in the presence of ≤2.5% impurity including (R)-Compound I-MsOH but excluding (S)-Compound III. In another embodiment, the disclosed synthesis of (S)-Compound I-MsOH results in the presence of ≤2.3% impurity including (R)-Compound I-MsOH but excluding (S)-Compound III. In some embodiments, the disclosed synthesis of (S)-Compound I-MsOH results in the presence of ≤2.0% impurity including (R)-Compound I-MsOH but excluding (S)-Compound III.

Process for the Synthesis of Compound V

Compound V, in some embodiments, represents boronic acids, boronic esters, pinacolboranes, boronic acid dimers, boronic acid trimers, mixtures thereof, or the like. It is commonly understood in the art that Compound V can be presented as various derivatives of boronic acids.

In some embodiments, dimethyl (4-(2-butoxyethoxy)phenyl)boronate (Compound V-OMe) is prepared by a Grignard formation of 1-bromo-4-(2-butoxyethoxy)benzene (Compound VI) and a subsequent reaction with trimethoxyborane.

It was discovered in a large scale batch that Grignard initiation was difficult. The previous process employed a dilute solution of Compound VI, approximately 50-70 parts tetrahydrofuran (THF) with respect to Compound VI. The initiation was very slow in the dilute solution of Compound VI with isopropylmagnesium chloride (iPrMgCl), which only occurred after prolonged reflux and addition of increased amounts of Compound VI, bringing the concentration to approximately 25 parts THF with respect to Compound VI. In addition to the difficulties in initiating the Grignard, it was found that the use of iPrMgCl had an adverse effect in the subsequent step (lower conversion of the Suzuki coupling step; see section Process for the synthesis of Compound II-OH).

To overcome the Grignard initiation issues, the activation step of the magnesium turnings, by heating and agitation, prior to the Grignard formation is necessary. In some embodiments, magnesium turnings were stirred for about 1 hour in about 9 parts of an ethereal solvent, such as THF. Subsequently, the solvent can be reduced to about 3 parts by distillation.

The Grignard initiation challenges, in some embodiments, are solved by using neat Compound VI to provide a more concentrated solution than the previous methods. In some embodiments, approximately 20% of the total amount of Compound VI is added neat to the solution of activated magnesium turnings over a period of at least 15 minutes, while the exotherm is controlled, such that the temperature of the reaction is maintained below the boiling point of the solvent. The resulting solution is heated at or around the boiling point of the solvent for about 1 hours to about 4 hours. The reaction mixture is then cooled by about 10° C. and diluted with the same solvent as used previously (5 parts). This disclosed Grignard initiation step, in some embodiments, results in the complete omission of iPrMgCl.

To the hot initiated Grignard solution, which is further diluted, the remaining Compound VI is slowly added neat over a period of about 30 minutes to about 1 hour. The addition of Compound VI is exothermic and the reaction mixture is carefully maintained to be well below the boiling point during the addition. The resulting mixture is stirred and heated to temperature below the boiling point of the solvent, for example about 55° C. for THF, for about 3 hours to about 4 hours. The heating time can be extended until high-performance liquid chromatography (HPLC) analysis indicates less than about 1% of Compound VI is remaining. It was noted that prolong heating time had no beneficial effect on the yield of the subsequent step or in the prevention of key impurity formations.

Previous process route for the synthesis of Compound V-OMe involved cooling the Grignard mixture to about −15° C. and adding a solution of trimethoxyborane in THF. The inventors discovered that this temperature range was not optimal and lead to lower yields and higher impurities. Also, it was found that the reaction was sensitive to the rate of addition of trimethoxyborane.

Considering the above findings, in some embodiments, Grignard mixture (once formation is complete) is cooled to about −25° C. and neat trimethoxyborane is added portionwise over about 2 hours. The reaction mixture was stirred at about −25° C. for about 1 hour to about 2 hours upon completion of the trimethoxyborane addition, then warmed up to about 20° C. and stirred for about 1 hour to about 2 hours to provide Compound V-OMe. In some embodiments, the neat trimethoxyborane was chilled prior to the addition to the Grignard mixture.

In some embodiments, the ratio of magnesium turning, Compound VI, and trimethoxyborane is about 1.08:1:1.

In some embodiments, anhydrous solvents are used in the synthesis of Compound V.

In other embodiments, the reaction for the synthesis of Compound V is maintained under atmospheric pressure of nitrogen or argon and the reaction vessels and equipment are rid of moisture prior to use.

In some embodiments, Compound VI and trimethoxyborane is both used as a neat solution to minimize reactor usage.

It was noted that filtration of the crude Compound V-OMe to remove excess magnesium and magnesium salts is not necessary as it had no effect on the subsequent step in terms of preventing key impurity formation.

Preparation of Compound V-OH

In some embodiments, Compound V is Compound V-OH. In one embodiment, Compound V-OH is synthesized by process known to one skilled in the art. In one embodiment, commercially available Compound V-OH (CAS No. 279262-28-1) is purified to obtain a crystalline Compound V-OH which is essentially free of Compounds V-A, V-B, and V-C.

In one embodiment, Compound V is Compound V-OH with ≤0.10% of Compound V-OH-A, Compound V-OH-B and/or Compound V-OH-C.

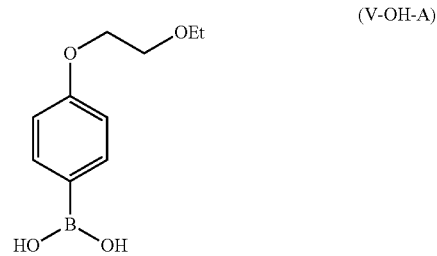

(V-OH-A)

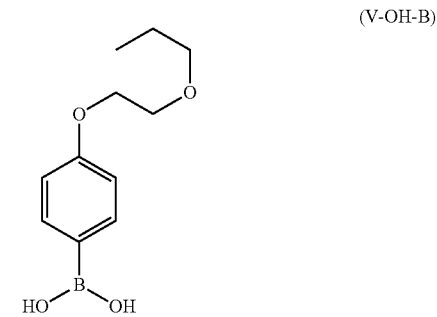

(V-OH-B)

-continued (V-OH-C)

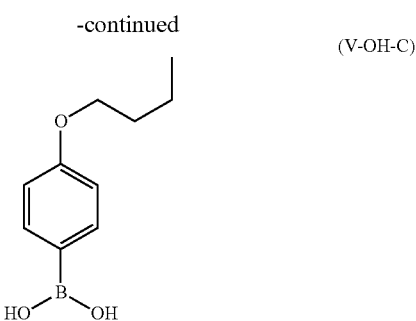

In some embodiments, Compound V-OH is dried such that the loss on drying (LOD) is below about 20%, about 19%, about 18%, about 17%, about 16%, about 15%, about 14%, about 13%, about 12%, about 11%, about 10%, about 9%, about 8%, about 7%, about 6%, or about 5%. In one embodiment, Compound V-OH is dried such that the loss on drying (LOD) is about 15%, about 14%, about 13%, about 12%, about 11%, or about 10%. In some embodiment, prolonged drying of Compound V-OH results in the formation of Compound V-3.

In one embodiment, Compound V-OH is about ≥85%, about ≥90%, about ≥95%, about ≥96%, about ≥97%, about ≥98%, or about ≥99% pure.

In other embodiments, dried sample of Compound V-OH can contain Compound V-3 in about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, or about 1%. In one embodiment, isolated crystalline Compound V-OH comprises Compound V-3 in less than about 5%, about 4%, about 3%, about 2%, about 1%, or about 0.5%.

In one embodiment, Compound V-3 is about ≥85%, about ≥90%, about ≥95%, about ≥96%, about ≥97%, about ≥98%, or about ≥99% pure.

In one embodiment, a mixture of dried Compound V-OH and Compound V-3 can be used in the reaction with Compound IV. In some embodiments, mixture of Compound V-OH and Compound V-3 can be in the ratio of about 1:99 to about 99:1. In other embodiments, the ratio of Compound V-OH and Compound V-3 can be about 5:95 to about 95:5. In one embodiment, the mixture of dried Compound V-OH and Compound V-3 is essentially free of Compounds V-A, V-B, and V-C. In other embodiments, the mixture of dried Compound V-OH and Compound V-3 comprises ≤0.10% of Compound V-OH-A, Compound V-OH-B and/or Compound V-OH-C.

In one embodiment, the mixture of Compound V-OH and Compound V-3 is about ≥85%, about ≥90%, about ≥95%, about ≥96%, about ≥97%, about ≥98%, or about ≥99% pure.

Process for the Synthesis of Compound II-OH

In some embodiments, Compound II-OH is prepared by the reaction between Compound IV and Compound V. In other embodiments, Compound II-OH is prepared by a transition metal-catalyzed process, such as a Suzuki coupling reaction, between Compound IV and Compound V. In one embodiment, the amount of Compound V used is about 1 equivalent (equiv) to about 3 equiv with respect to Compound IV. In other embodiments, the amount of Compound V used is about 2 equiv with respect to Compound IV.

A previous process for the synthesis of Compound II-OH also involved a Suzuki coupling reaction where the reaction mixture containing Compound V was charged with palladium acetate (Pd(OAc)$_2$) catalyst and triphenylphosphine ligand (PPh$_3$), prior to the addition of aqueous base solution (water and solid base). This synthetic route yielded Compound II-OH in a moderate yield of about 55% to about 64% yield with purity ranging from about 92% to about 99%.

It was discovered that, in some embodiments, the addition of the aqueous base solution to form a biphasic mixture prior to the addition of the palladium (Pd) catalyst and the ligand is beneficial in reducing Compound VII impurity, resulting from homo-coupling of Compound V. In some embodiments, a solution of a base in about 6.5 parts water is added to the reaction mixture containing Compound V, prepared as described previously. In other embodiments, base may be selected from the group consisting of alkali carbonates (potassium carbonate, sodium carbonate, cesium carbonate, etc), alkali metal hydrogen carbonates (potassium bicarbonate, sodium bicarbonate, etc), alkaline metal acetates (potassium acetate, sodium acetate, etc), alkaline metal phosphates (potassium phosphate, sodium phosphate, etc), alkali metal fluorides (potassium fluoride, cesium fluoride, etc), alkaline metal alkoxides (potassium tert-butoxide, sodium tert-butoxide, etc), alkali metal hydroxides (potassium hydroxide, sodium hydroxide, etc), and organic bases such as alkyl amines (triethylamine, diisopropylamine, diisopropylethyl amine, etc) pyridines (pyridine, dimethylaminopyridine, etc), cyclic amines (morpholine, 4-methylmorpholine, etc), and the combination thereof. In one embodiment, the base is potassium carbonate (K$_2$CO$_3$). In some embodiments, the equivalent of base is about 1 equiv to about 8 equiv with respect to Compound IV.

The addition of the aqueous base solution, in some embodiments, is carried out over a period of at least 30 minutes to at least 1 hour. The slow addition of the base solution was found critical in the yield of the Suzuki coupling reaction. Without being bound to any theory, this is presumably due to the prevention of salt formation during the biphasic mixture formation.

Previous synthetic routes of the Suzuki coupling reaction raised issues regarding reaction conversion when carried out in a large scale. It was discovered that purging the biphasic reaction mixture with nitrogen (N$_2$), by bubbling N$_2$ directly into the reaction mixture, for about 1 hour to rid air content, such as oxygen, provided the desired reaction conversion. This process is known as the degassing. Degassing the reaction mixture was also found beneficial in reducing Compound VII impurities from the Suzuki coupling step.

In some embodiments, to a degassed biphasic reaction mixture containing Compound V, a Pd-catalyst and a ligand is added. Previous synthetic route utilized tetrakis(triphenylphosphine) palladium (Pd(PPh$_3$)$_4$) catalyst system achieved by adding Pd(OAc)$_2$ and PPh$_3$. The yield of the Suzuki reaction using Pd(PPh$_3$)$_4$ catalyst system was not optimal as represented by the moderate yield of Compound II-OH (about 55% to about 64% yield).

Further optimization of the catalyst system was undertaken to improve yields and to lower Compound VIII impurity. As described in Example 1 and Table 1, optimization of the Pd(PPh$_3$)$_4$ catalyst system demonstrated that good conversion was achieved only when catalyst loading was significantly increased (from about 2 mol % to about 10 mol %, Table 1 entry 6) or when the reaction was refluxed substantially longer time (about 27 hours, entry 5). It was also noted that when high catalyst loading was employed, the amount of Compound VIII impurity was significantly lower (0.04%, entry 6); however, high catalyst loading interfered with the crystallization of the product. Also, lowering the temperature for the Suzuki coupling reaction showed unsuccessful in preventing Compound VIII impurity.

Next, different catalyst systems were considered as shown in Example 2 and Table 2. Removal of the phosphine ligands (Table 2, entry 1) was shown detrimental to the reaction conversion. The inventors discovered that catalyst system of $Pd(OAc)_2/P(o\text{-tol})_3$ increased reaction yield (about 80-85%) and product purity (>99%) compared to the previous $Pd(PPh_3)_4$ catalyst system. Furthermore, with the newly discovered $Pd(OAc)_2/P(o\text{-tol})_3$ catalyst system, the catalyst loading could be minimized significantly from about 2 mol % to about 0.25 mol %. It was also noted that with the disclosed catalyst system, degassing the reaction did not affect conversion rate, purity of the product, or the amount of Compound VIII. The catalyst optimization study from Examples 1-2 both indicate the amount of Compound VIII impurity has very little to no correlation with the Suzuki coupling reaction conditions.

In some embodiments, Pd-catalyst and ligands are added to the reaction biphasic reaction mixture containing Compound V. In some embodiments, Pd-catalyst can be a Pd(0) species or a Pd(II) species. Non-limiting examples of Pd-catalyst include tetrakis(triphenylphosphine) palladium (Pd (PPh$_3$)$_4$), tri(dibenzylideneacetone) dipalladium, bis(tri-t-butylphosphine) palladium, bis[1,2-bis(diphenylphophino) ethane]palladium, bis(tricyclohexylphosphine) palladium, palladium acetate (Pd(OAc)$_2$), palladium chloride (PdCl$_2$), dichlorobis(triphenylphosphine) palladium, palladium acetylacetonate, palladium bromide, palladium iodide, palladium cyanide, palladium hydroxide, palladium nitrate, tetraammine palladium(II) chloride hydrate, dinitrodiammine palladium, di-µ-chlorobis(η-allyl) palladium, dichlorobis(benzonitrile) palladium, dichlorobis(acetonitrile) palladium, palladium propionate, [1,1'-bis(diphenylphosphino) ferrocene]palladium(II) chloride, tetrakis(tri-o-tolylphosphine) palladium, tetrakis(tri-t-butylphosphine) palladium, bis(1,2-bis(diphenylphosphino)ethane) palladium, bis(1,1'-bis(diphenylphosphino)ferrocene) palladium, tetrakis(triethylphosphite) palladium, and combinations thereof.

In some embodiments, the ligand is selected from the group consisting of phosphine ligands (tritolylphosphine, triphenylphosphine, trimethylphosphine, triethylphosphine, trimethylphosphite, triethylphosphite, tri-n-butylphosphite, tri-tert-butylphosphine, di-tert-butylmethylphosphine, etc), nitrogen based ligands (pyridine, bipyridine, etc), NHC ligands (N,N'-bis(2,6-diisopropylphenyl)imidazol-2-ylidene etc), and combinations thereof.

In some embodiments, the Pd-catalyst/ligand system is $Pd(OAc)_2/P(o\text{-tol})_3$. In other embodiments, the Pd-catalyst and the ligand are added with continuous degassing of the reaction mixture.

In some embodiments, the amount of Pd-catalyst used is about 0.001 mol % to about 10.0 mol % with respect to Compound IV. In one embodiment, the amount of Pd-catalyst used is about 0.05 mol % to about 0.25 mol % with respect to Compound IV.

In some embodiments, the ratio of the ligand to the Pd-catalyst is about 1:1 to about 3:1. In some embodiments, the ratio of the ligand to the Pd-catalyst is about 2:1.

In some embodiments, Compound IV is added to the biphasic mixture containing Compound V and Pd-catalyst/ligand system. In one embodiment, Compound IV is added with continuous degassing of the reaction mixture.

In some embodiments, the reaction mixture upon the addition of Compound IV is heated for about 2 hours to about 5 hours and then cooled to ambient temperature. In some embodiments, the reaction mixture is heated to no greater than 65° C. It was noted that Pd-catalyst becomes inactive when temperature is raised above 65° C. For example, a Suzuki reaction set at a temperature of 90° C. did not go to completion. In one embodiment, the reaction was heated until HPLC analysis indicates ≤2% Compound IV remaining and indicates formation of Compound II-OH.

Once the reaction was deemed complete by HPLC, in some embodiments, the reaction is cooled to ambient temperature and the pH of the reaction mixture was adjusted to about 2.0 to about 3.0 using aqueous acid solutions. In some embodiment, hydrochloric acid (HCl) is used.

In some embodiments, Compound V is Compound V-OMe.

In some embodiments, Compound V is Compound V-OH. In one embodiment, commercially available Compound V-OH (CAS No. 279262-28-1) is purified to obtain a crystalline Compound V-OH which is essentially free of Compounds V-A, V-B, and V-C.

In some embodiment, Compound V is Compound V-OH with ≤0.10% of Compound V-OH-A, Compound V-OH-B and/or Compound V-OH-C. In one embodiment, Compound V-OH comprises one or both of: (a) about ≤0.01% of Compound II-OH-A; and (b) about ≤0.01% of Compound II-OH-B; and optionally further comprises about ≤0.10% of Compound II-OH-C. In another embodiment, Compound V-OH comprises (a) about ≤0.01% of Compound II-OH-A; (b) about ≤0.01% of Compound II-OH-B; and (c) about ≤0.10% of Compound II-OH-C.

In one embodiment, isolated Compound V-OH is crystalline.

In one embodiment, Compound V-OH comprises less than about 15%, less than about 10%, or less than about 5% Compound V-3.

In one embodiment, Compound V-3 is used instead of Compound V-OMe or Compound V-OH. In another embodiment, Compound V-3 is used as a mixture of Compound V-OH. In one embodiment, Compound V-3 is essentially free of Compounds V-A, V-B, and V-C. In other embodiment, Compound V-3 comprises ≤0.10% of Compound V-OH-A, Compound V-OH-B and/or Compound V-OH-C. In one embodiment, Compound V-3 comprises one or both of: (a) about ≤0.01% of Compound II-OH-A; and (b) about ≤0.01% of Compound II-OH-B; and optionally further comprises about ≤0.10% of Compound II-OH-C. In another embodiment, Compound V-3 comprises (a) about ≤0.01% of Compound II-OH-A; (b) about ≤0.01% of Compound II-OH-B; and (c) about ≤0.10% of Compound II-OH-C.

In one embodiment, dried Compound V-3 comprises less than about 25%, less than about 20%, less than about 15%, less than about 10%, or less than about 5% Compound V-OH.

In one embodiment, isolated Compound V-3 is crystalline.

Purification of Compound II-OH

Previous purification process for Compound II-OH required two hot recrystallizations and two charcoal treatments. The disclosed purification process, in some embodiments, requires one charcoal treatment, one anti-solvent recrystallization, and/or one hot recrystallization.

In one embodiment the improvement in purity of Compound II-OH from previous synthesis methods which led to reduction number of steps for purification of Compound II-OH is attributed to the use of isolated Compound V-OH and/or Compound V-3 in the reaction with Compound IV. In one embodiment, the improvement in purity of Compound II-OH from previous synthesis methods which led to reduction of number of steps for purification of Compound II-OH is attributed to the use of crystalline, isolated Compound V-OH and/or Compound V-3 in the reaction with Compound IV. In a further embodiment, the isolated Compound V-OH and/or Compound V-3 or the crystalline, isolated Compound V-OH and/or Compound V-3 is essentially free of Compounds V-A, V-B, and V-C.

In one embodiment, the improvement in purity of compound II-OH from previous synthesis methods which led to reduction number of steps for purification of Compound II-OH is attributed to the use of isolated Compound V-OH in the reaction with Compound IV.

The acidified biphasic reaction mixture containing crude Compound II-OH is, in some embodiments, separated into an aqueous layer and an organic layer. In some embodiments, the resulting aqueous layer is extracted with an organic solvent. In one embodiment, the aqueous layer is extracted with toluene (about 10 parts).

The volume of the combined organic layers is, in some embodiments, reduced to about 6.5 parts. In some embodiments, the volume of the combined organic layer is reduced by distillation. The resulting reduced organic layer is, in some embodiments, treated with charcoal. In other embodiments, the resulting reduced organic layer is treated with charcoal and Celite®. In one embodiment, the ratio of charcoal to Celite® is about 1:2 by weight. The reaction mixture containing charcoal is, in some embodiment, stirred for about 1 hour to about 5 hours at an ambient temperature. The charcoal is then, in other embodiments, filtered and the volume of the reaction is reduced to about 3 parts. In one embodiment, the volume is reduced by distillation.

In some embodiments, antisolvent recrystallization is used for purification of Compound II-OH. To the reduced crude mixture, polar solvents, such as isopropanol and ethyl acetate, is added and concentrated to an oil. In one embodiment, a non-polar antisolvent is added over a period of about 1 hour, portion wise, to the crude oil mixture. The resulting suspension was stirred at ambient temperature for about 1 hour to about 8 hours. In some embodiments, the precipitated crystals are then collected by filtration. In some embodiments, the mother liquor is not recirculated to remove any remaining crystals from the reaction vessels; instead multiple solvent wash may be added using fresh solvents.

In some embodiments, the antisolvent is heptanes. In other embodiments, the polar solvent is isopropanol or a mixture of isopropanol and ethyl acetate. In some embodiments, the product precipitates without the addition of the antisolvent.

In some embodiments, a hot recrystallization is used for purification of Compound II-OH. The crude material containing Compound II-OH or crude crystals of Compound II-OH are dissolved in polar solvents such as isopropanol and ethyl acetate at an elevated temperature. The temperature of the solution is slowly reduced to ambient temperature and stirred until recrystallization is complete and then the crystals are collected by filtration.

In some embodiments, the polar solvent used is isopropanol or isopropanol and ethyl acetate mixture. In some embodiments, the crude Compound II-OH is dissolved in mixture of isopropanol and ethyl acetate in about 9:1 ratio at about 70° C. In other embodiments, the temperature of the hot solution is decreased by about 10° C. every about 1 hour until it reaches ambient temperature. In some embodiments, once the solvent is cooled to an ambient temperature, the solution is stirred for about 2 hours to about 6 hours. The resulting crystals are, in some embodiments, collected by filtration. In some embodiments, the mother liquor is not recirculated to remove any remaining crystals from the reaction vessels; instead multiple solvent wash may be added using fresh solvents.

Recrystallization solvent study revealed that when hot recrystallization is carried out in isopropanol alone, the recovery of Compound II-OH was high (90-93%) and decreased impurity Compound VIII by about 50-60%. When hot recrystallization is carried out in ethyl acetate alone, the recovery of Compound II-OH was lower (70-75%) than isopropanol system but the reduction in impurity Compound VIII was greater (by 80-83%). When hot recrystallization is carried out in a mixture of isopropanol and ethyl acetate, both high recovery of Compound II-OH (90-92%) and effective reduction in impurity Compound VIII (by 75-80%) was obtained.

In some embodiments, both antisolvent recrystallization and hot recrystallization is utilized. In some embodiments, the combination of antisolvent recrystallization and hot recrystallization reduces impurity Compounds VIII and IX significantly. In some embodiments, recrystallization steps can be repeated to reach the desired purity. In one embodiment, following the disclosed process for the synthesis of Compound II-OH as described herein, the purity of Compound II-OH is about ≥95.0% to about ≤96.0% or ≥97.0%, with one or both of about ≤0.50% to about ≥0.30% of Compound VII, and about ≤0.50% to about ≥0.30% of Compound VIII, and optionally further comprises about ≤0.50% of Compound IX. In one embodiment, following the disclosed process for the synthesis of Compound II-OH as described herein, the purity of Compound II-OH is about ≥95.0% to about ≤96.0% or ≥97.0%, with about ≤0.50% to about ≥0.30% of Compound VII, with about ≤0.50% to about ≥0.30% of Compound VIII, and with about ≤0.50% of Compound IX. In other embodiments, following the disclosed process for the synthesis of Compound II-OH as described herein, the purity of Compound II-OH is about ≥95.0% to about ≤96.0%, with about ≤0.20% of Compound VII, with about ≤0.20% of Compound VIII, and with about ≤0.50% of Compound IX. In some embodiments, following the disclosed process for the synthesis of Compound II-OH as described herein, the purity of Compound II-OH is about ≥95.0% to about ≤96.0%, with about ≤0.10% of Compound VII, with about ≤0.10% of Compound VIII, and with about ≤0.25% of Compound IX. In one embodiment, following the disclosed process for the synthesis of Compound II-OH as described herein, the purity of Compound II-OH is about ≥95.0% to about ≤96.0%, with about ≤0.05% of Compound VII, with about ≤0.05% of Compound VIII, and with about ≤0.15% of Compound IX. In one embodiment, following the disclosed process for the synthesis of Compound II-OH as described herein, the purity of Compound II-OH is about ≥95.0% to about ≤96.0% or ≥97.0%, with about ≤0.01% of Compound VIII, and optionally further comprises one or both of about ≤0.05% of Compound VII, and about ≤0.15% of Compound IX. In one embodiment, following the disclosed process for the synthesis of Compound II-OH as described herein, the purity of Compound II-OH is about ≥95.0% to about ≤96.0% or >97.0%, with about ≤0.05% of Compound VII, with about ≤0.01% of Compound VIII, and with about ≤0.15% of Compound IX.

In one embodiment, following the disclosed process for the synthesis of Compound II-OH as described herein, the purity of Compound II-OH is about ≥95.0% to about ≤96.0% or >97.0%, with one or both of about ≤0.50% to about ≥0.30% of Compound II-OH-A, and about ≤0.50% to about ≥0.30% of Compound II-OH-B, and optionally further comprises about ≤0.50% of Compound II-OH-C. In one embodiment, following the disclosed process for the synthesis of Compound II-OH as described herein, the purity of Compound II-OH is about ≥95.0% to about ≤96.0% or >97.0%, with about ≤0.50% to about ≥0.30% of Compound II-OH-A, with about ≤0.50% to about ≥0.30% of Compound II-OH-B, and with about ≤0.50% of Compound II-OH-C. In one embodiment, following the disclosed process for the synthesis of Compound II-OH as described herein, the purity of Compound II-OH is about ≥95.0% to about ≤96.0%, with about ≤0.20% of Compound II-OH-A, with about ≤0.20% of Compound II-OH-B, and with about ≤0.50% of Compound II-OH-C. In another embodiment, following the disclosed process for the synthesis of Compound II-OH as described herein, the purity of Compound II-OH is about ≥95.0% to about ≤96.0%, with about ≤0.10% of Compound II-OH-A, with about ≤0.10% of Compound II-OH-B, and with about ≤0.25% of Compound II-OH-C. In some embodiments, following the disclosed process for the synthesis of Compound II-OH as described herein, the purity of Compound II-OH is about ≥95.0% to about ≤96.0%, with about ≤0.05% of Compound II-OH-A, with about ≤0.05% of Compound II-OH-B, and with about ≤0.15% of Compound II-OH-C. In some embodiments, following the disclosed process for the synthesis of Compound II-OH as described herein, the purity of Compound II-OH is about ≥95.0% to about ≤96.0% or >97.0%, with one or both of about ≤0.01% of Compound II-OH-A, and about ≤0.01% of Compound II-OH-B, and optionally further comprises about ≤0.10% of Compound II-OH-C. In some embodiments, following the disclosed process for the synthesis of Compound II-OH as described herein, the purity of Compound II-OH is about ≥95.0% to about ≤96.0% or ≥97.0%, with about ≤0.01% of Compound II-OH-A, with about ≤0.01% of Compound II-OH-B, and with about ≤0.10% of Compound II-OH-C.

Preparation of Compound I

The previous process for preparing Compound I and subsequently Compound I-MsOH presented challenges with the presence of Compound II-OH (starting material) in the final product. It was discovered that the formation of Compound II-OH is dependent on several steps or features of the reaction. First, the formation of acid chloride Compound II-Cl (Compound II where $R_1$=Cl). Second, the solvent choice of the reaction affected the amount of Compound II-OH produced. Third, is regarding the salt formation step. The disclosed process, described herein, addresses these challenges and describes protocols that reduce the formation of Compound II-OH significantly.

In some embodiments, Compound I is synthesized by a reaction between Compound II and Compound III. In some embodiments, Compound II-OH is reacted with a chlorinating reagent to form Compound II-Cl. In some embodiments, Compound II-Cl reacts with Compound III to produce Compound I.

In some embodiments, Compound II-OH is dissolved in a solvent and a chlorinating reagent is added to yield Compound II-Cl. In some embodiments, the solvent used include, but are not limited to, tetrahydrofuran (THF), dimethylforamide (DMF), diethylether, and methylene chloride (DCM). In one embodiment, the solvent is methylene chloride.

Previous process utilized THF as the solvent for the acid chloride formation with the addition of DMF. It was discovered that the formation of Compound II-OH could be minimized when DCM is used as the solvent for the acid chloride formation.

Prior to the addition of the chlorinating reagent, the solution containing Compound II-OH is cooled below ambient temperature. In some embodiments, the solution containing Compound II-OH is cooled to about 10° C. to about 15° C. In some embodiments, the chlorinating reagent is added over about 10 minutes to about 30 minutes while the temperature of the solution was maintained below ambient temperature. In some embodiments, the mixture is maintained at about 10° C. to about 15° C. and stirred for about 2 hours to about 4 hours then cooled to about 0° C. or below. In one embodiment, the reaction was stirred until HPLC analysis indicated ≤3.0% of Compound II-OH is present.

Non-limiting examples of chlorinating reagents include thionyl chloride, phosphorous trichloride, phosphorus pentachloride, phosphorus oxychloride, oxalyl chloride, phosgene, and the like or the combinations thereof. In one embodiment, the chlorinating reagent is thionyl chloride. In another embodiment, the chlorinating reagent is used in about 1.0 equiv to about 2.0 equiv with respect to Compound II-OH. In one embodiment, the chlorinating reagent is used in about 1.0 equivalent to about 1.1 equiv with respect to Compound II-OH. In another embodiment, the ratio of the chlorinating reagent and the Compound II-OH is about 1:1.

In a separate reaction vessel, Compound III is dissolved in a solvent with a base. To the solution of Compound III and a base, a solution of Compound II-Cl is slowly added. In some embodiment, the solvent used for dissolving Compound III can be tetrahydrofuran, dimethylforamide, diethylether, methylene chloride, and mixtures thereof. In one embodiment, the solvent is methylene chloride. In some embodiments, the reaction is cooled to about 0° C. before the addition of Compound III. In one embodiment, the reaction is maintained at about 0° C. for about 3 hours to about 7 hours after the addition of Compound III until HPLC analysis indicates ≤0.5% of Compound II-Cl is present. In another embodiment, Compound III is used in about 1.0 equiv to about 1.2 equiv with respect to Compound II-OH.

In some embodiments, the base is used in about 1 equiv to about 4 equiv. Non-limiting example of base includes alkali carbonates (potassium carbonate, sodium carbonate, cesium carbonate, etc), alkali metal hydrogen carbonates (potassium bicarbonate, sodium bicarbonate, etc), alkaline metal acetates (potassium acetate, sodium acetate, etc), alkaline metal phosphates (potassium phosphate, sodium phosphate, etc), alkali metal fluorides (potassium fluoride, cesium fluoride, etc), alkaline metal alkoxides (potassium tert-butoxide, sodium tert-butoxide, etc), alkali metal hydroxides (potassium hydroxide, sodium hydroxide, etc), and organic bases such as alkyl amines (triethylamine, diisopropylamine, diisopropylethyl amine, etc) pyridines (pyridine, dimethylaminopyridine, etc), cyclic amines (morpholine, 4-methylmorpholine, etc), and the combinations thereof. In one embodiment, the base is pyridine. In some embodiments, pyridine reacts with Compound II-Cl to form pyridine-HCl salt and vigorous agitation may be necessary to prevent aggregation of the salt.

Upon the indication of the conversion of Compound II-Cl to Compound I, the reaction mixture is, in one embodiment, acidified. In some embodiments, citric acid solution is used to acidify the reaction mixture containing crude Compound I. In one embodiment, citric acid is used in about 1.5 equiv to about 2.0 equiv in about 10 parts water with respect to Compound II-OH and added over about 30 minutes to about 1 hour. In one embodiment, a chilled citric acid aqueous solution is added to a cooled reaction mixture while maintaining an internal temperature of about 0° C.

In some embodiments, the volatile solvent is removed to provide a total volume of about 13 parts. In other embodiments, a different solvent is added (about 5 parts) to the reduced reaction mixture, and reduced once again to provide a total volume of about 13 parts. In some embodiments, a polar solvent such as ethyl acetate is used. In other embodiment, the solvent is removed under reduced pressure.

The reduced reaction mixture which consists of a majority of an acidic aqueous layer, in some embodiments, is extracted with a polar solvent such as ethyl acetate in about 10 parts. In some embodiments, the organic layer containing the desired product, Compound I, is washed with aqueous solutions several times, for example with a solution of sodium bicarbonate and brine.

The stability of Compound I during workup procedure was studied. It was demonstrated that Compound I is not particularly sensitive to light during workup and the use of clear reaction vessel or an amber reaction vessel did not display increased hydrolysis of Compound I to Compound II-OH. Additionally, Compound I was studied in various pH and temperature during workup procedures; however, no correlation was discovered for increased hydrolysis of Compound I to Compound II-OH. Although it is still a possibility that Compound I can hydrolyze to Compound II-OH during workup, the amide bond is fairly stable under the workup conditions.

Water content in the organic layer resulting from the extraction workup is found to have an impact on the overall yield of the salt formation of Compound I (Compound I-MsOH). In some embodiments, the presence of water during the salt formation increased the hydrolysis of Compound I back to Compound II-OH, thus a rigorous drying process is ideal. In some embodiments, the organic layer, containing Compound I, is dried with 3 Å powdered molecular sieves. In some embodiments, the resulting slurry is stirred for about 15 hours to about 30 hours at an ambient temperature before the molecular sieves are removed by filtration. The filtered molecular sieves are washed with a polar solvent such as ethyl acetate. In some embodiments, the residual water content is determined by titration. In some embodiments, the drying step using molecular sieves can be repeated until the residual water is ≤2.5%.

Once the organic layer containing Compound I is dried and determined to be substantially free of water, in some embodiments, the solvent is removed to give a total volume of about 3 parts. In some embodiments, the solvent is removed by distillation. In other embodiment, the solution is assayed by HPLC before or after the solvent reduction to calculate the amount of Compound I present.

Alternatively, in one embodiment, Compound I is synthesized from Compound II and Compound III using coupling reaction conditions commonly known in the art, using reagents including but are not limited to carbodiimides, 1-hydroxybenzotriazole, hydroxy-3,4-dihydro-4-oxo-1,2,3-benzotriazine, N-hydroxysuccinimide, 1-hydroxy-7-aza-1H-benzotriazole, 2-(1H-Benzotriazol-1-yl)-N,N,N',N'-tetramethylaminium tetrafluoroborate/hexafluorophosphate, 2-(6-Chloro-1H-benzotriazol-1-yl)-N,N,N',N'-tetramethylaminium hexafluorophosphate, and/or 2-(7-Aza-1H-benzotriazol-1-yl)-N,N,N',N'-tetramethylaminium hexafluorophosphate, 2-propanephosphonic acid anhydride, and 1,1'-carbonyldiimidazole.

Preparation of Compound I-MsOH

To the concentrated crude solution of Compound I, in some embodiments, a solvent is added in about 4 parts. In one embodiment, the solvent used is acetonitrile. To the solution containing Compound I, methane sulfonic acid (MsOH) is added. In some embodiments, MsOH is added in a single portion. In other embodiments, MsOH is used in about 0.9 equiv to about 1.5 equiv with respect to Compound I as determined by the HPLC assay. In one embodiment, MsOH is used in about 0.97 equiv to about 1.02 equiv.

In some embodiments, MsOH is washed into solution containing Compound I and MsOH with additional solvent such as acetonitrile or ethyl acetate. The reaction mixture is stirred at an ambient temperature for about 30 minutes to about 1 hour. It was discovered that excess MsOH had an adverse effect on the formation of Compound II-OH by hydrolysis of the amide bond of Compound I, therefore an accurate assay of Compound I is critical to determine the exact amount of Compound I present and the exact amount of MsOH required to achieve a 1:1 stoichiometric ratio during salt formation. In one embodiment, Compound I and MsOH are used in 1:1 ratio to minimize amide bond hydrolysis.

In one embodiment, the solvent used in the step of converting Compound I into Compound I-MsOH, is free of alcohol solvents. It was discovered that residual levels of alcohol solvents (e.g., methanol, ethanol, etc.) in the reaction lead to contamination of Compound I-MsOH with mesylate esters. These resulting mesylate esters are known mutagens.

In some embodiments, prior to crystallization, the reaction mixture was washed with brine and dried using 3 Å molecular sieves. In some cases, it was determined that slight amount of water present in the reaction mixture could prevent crystallization to occur and/or result in lower yield of Compound I-MsOH. Not wishing to be bound by any theory, the lower yield resulted in systems with higher water content is due to higher hydrolysis rate to give Compound II-OH which was found in the mother liquor at a higher concentration in a study with higher water content.

To crystalize Compound I-MsOH from the reaction mixture, in some embodiments, a pure sample of Compound I-MsOH is used as a seed. The solution, with or without seeding, is in some embodiments, stirred at an ambient temperature for about 6 hours to about 10 hours. Additionally, in some embodiments, the solution is stirred at about 0° C. for about 6 hours to about 10 hours. The precipitated crystals are, in some embodiments, collected by filtration. In some embodiments, the crystals are washed with cold solvent such as ethyl acetate to obtain crude Compound I-MsOH.

The crude crystals of Compound I-MsOH are, in some embodiments, further purified using hot recrystallization technique. In some embodiments, crystals of Compound I-MsOH are dissolved in solvents (about 10 parts) at an elevated temperature. In other embodiments, crystals of Compound I-MsOH are dissolved in acetonitrile at about 70° C. The hot solution of Compound I-MsOH was slowly cooled to about 50° C. to about 55° C. over a period of about 1 hour. In some embodiments, the solution of Compound I-MsOH was seeded with pure sample of Compound I-MsOH at about 50° C. to about 55° C. The solution, with or without seeding, is stirred at about 50° C. to about 55° C. for about 4 hours to about 8 hours, in some embodiments. The hot solution is, in some embodiments, cooled to an ambient temperature over about 1 hour and stirred at an ambient temperature for about 6 hours to about 10 hours. In one embodiment, hot recrystallization of Compound I-MsOH from acetonitrile reduces contamination, including mesylate esters.

The precipitated crystals of Compound I-MsOH, in some embodiments, are collected by filtration. In other embodiments, the filtered crystals of Compound I-MsOH are washed with acetonitrile. In one embodiment, the filtered crystals of Compound I-MsOH are washed with cold acetonitrile. The purity of the crystals is assayed by titration and HPLC. If necessary, hot recrystallization can be repeated until the desired purity is obtained. In some embodiments, the filtered crystals of Compound I-MsOH are dried under reduced pressure. In other embodiments, the dried crystals are further pulverized by a powder mill and a jet mill or the like.

The study of the Compound I-MsOH crystals under a microscope revealed that the surface of the crystals became oily with time, which is identified as a result of hydrolysis on the surface of the crystals. Acetonitrile was found to be a solvent that Compound II-OH is more soluble in than Compound I-MsOH. Therefore, upon recrystallization, it is beneficial to wash the filtered crystals with acetonitrile. Due to Compound I-MsOH also being soluble in acetonitrile to some degree, in some embodiments, cold acetonitrile should be used to wash the crystals, and the volume and the frequency of the wash should be limited to about twice with about 2 parts volume to about 3 parts volume.

The hydrolysis of Compound I or Compound I-MsOH is susceptible in the presence of water or acid. In some embodiments, the reaction mixture should be substantially free of water prior and during purification steps of Compound I-MsOH. In other embodiments, the reaction mixture should be substantially free of aqueous acid prior and during purification steps of Compound I-MsOH. In some embodiments, gentle agitation should be maintained through the salt formation and purification steps of Compound I-MsOH.

In some embodiments, Compound III used in the reaction to obtain Compound I or Compound I-MsOH is optically pure. In which case, it will result in an optically pure Compound I or optically pure Compound I-MsOH. In one embodiment, Compound III is (S)-Compound III. In another embodiment, Compound I-MsOH is (S)-Compound I-MsOH.

The disclosed process of the synthesis of Compound II-OH and its subsequent use in the disclosed process of the synthesis of Compound I-MsOH, in some embodiments, results in highly pure Compound I-MsOH that is substantially free of Compounds I-MsOH-A, I-MsOH-B, I-MsOH-C, I-MsOH-D, I-MsOH-E, I-MsOH-F, I-MsOH-G, II-OH, III, VI, VII, VIII, IX, and mesylate esters resulting from MsOH. In some embodiments, Compound I-MsOH, e.g., synthesized by the disclosed process, disclosed herein will result in >96% purity. In other embodiments, Compound I-MsOH, e.g., synthesized by the disclosed process, disclosed herein will result in >97% purity. In one embodiment, Compound I-MsOH, e.g., synthesized by the disclosed process, disclosed herein will result in >98% purity. In another embodiment, Compound I-MsOH, e.g., synthesized by the disclosed process, disclosed herein will result in >99% purity.

The disclosed process of the synthesis of Compound II-OH and its subsequent use in the disclosed process of the synthesis of Compound I-MsOH, in some embodiments, results in highly pure (S)-Compound I-MsOH that is substantially free of (R)-Compound I-MsOH, R or S versions of (I-MsOH-A, I-MsOH-B, I-MsOH-C, I-MsOH-D, I-MsOH-E, I-MsOH-F, I-MsOH-G), II-OH, III, VI, VII, VIII, IX, and mesylate esters resulting from MsOH. In some embodiments, (S)-Compound I-MsOH, e.g., synthesized by the disclosed process, disclosed herein will result in >96% purity. In other embodiments, (S)-Compound I-MsOH, e.g., synthesized by the disclosed process, disclosed herein will result in >97% purity. In one embodiment, (S)-Compound I-MsOH, e.g., synthesized by the disclosed process, disclosed herein will result in >98% purity. In another embodiment, (S)-Compound I-MsOH, e.g., synthesized by the disclosed process, disclosed herein will result in >99% purity.

In other embodiments, Compound I-MsOH, e.g., synthesized by the disclosed process, will contain ≤0.2% of each impurities including Compounds I-MsOH-A, I-MsOH-B, I-MsOH-C, I-MsOH-F, I-MsOH-G, VII, VIII, and IX. In other embodiments, Compound I-MsOH, e.g., synthesized by the disclosed process, will contain ≤1.0%, ≤0.8%, ≤0.6%, or ≤0.4% of each impurities including I-MsOH-D and Compound II-OH. In other embodiments, Compound I-MsOH, e.g., synthesized by the disclosed process, will contain ≤1,500 ppm of Compound III. In another embodiment, Compound I-MsOH, e.g., synthesized by the disclosed process, will contain ≤0.3% of each impurities including Compounds I-MsOH-C, I-MsOH-E, and I-MsOH-F. In some embodiments, Compound I-MsOH, e.g., synthesized by the disclosed process, will contain ≤0.002% (20 ppm) mesylate ester resulting from MsOH. In some embodiments, Compound I-MsOH contains ≤0.002% (20 ppm) mesylate ester for a 150 mg dose. In some embodiments, Compound I-MsOH contains ≤15 ppm mesylate ester for a 150 mg dose. In one embodiment, Compound I-MsOH contains ≤0.001% (10 ppm) mesylate ester for a 150 mg dose.

In other embodiments, Compound I-MsOH, e.g., synthesized by the disclosed process, will contain ≤0.3% of each impurities including Compounds I-MsOH-A, I-MsOH-B, I-MsOH-C, I-MsOH-F, I-MsOH-G, VII, VIII, and IX. In other embodiments, Compound I-MsOH, e.g., synthesized by the disclosed process, will contain ≤0.5% of each impurities including I-MsOH-D and Compound II-OH. In other embodiments, Compound I-MsOH, e.g., synthesized by the disclosed process, will contain ≤1,000 ppm of Compound III. In another embodiment, Compound I-MsOH, e.g., synthesized by the disclosed process, will contain ≤0.15% of each impurities including Compounds I-MsOH-C, I-MsOH-E, and I-MsOH-F, VII, VIII, and IX. In some embodiments, Compound I-MsOH, e.g., synthesized by the disclosed process, will contain ≤0.001% (10 ppm) mesylate ester resulting from MsOH.

In other embodiments, Compound I-MsOH, e.g., synthesized by the disclosed process, will contain ≤0.05% of each impurities including Compounds I-MsOH-A, I-MsOH-B, I-MsOH-C, I-MsOH-F, I-MsOH-G, VII, VIII, and IX. In other embodiments, Compound I-MsOH, e.g., synthesized by the disclosed process, will contain ≤0.30% of each impurities including Compound I-MsOH-D and Compound II-OH. In some embodiments, Compound I-MsOH, e.g., synthesized by the disclosed process, will contain ≤0.1% of each impurities including I-MsOH-A, I-MsOH-B, I-MsOH-C, I-MsOH-F, I-MsOH-G, VII, VIII, and IX. In other embodiments, Compound I-MsOH, e.g., synthesized by the disclosed process, will contain ≤0.15% of each impurities including Compound I-MsOH-D and Compound II-OH. In some embodiments, (S)-Compound I-MsOH, e.g., synthesized by the disclosed process, will contain ≤1.0% of (R)-Compound I-MsOH. In another embodiment, (S)-Compound I-MsOH, e.g., synthesized by the disclosed process, will contain ≤0.5% of (R)-Compound I-MsOH. In one embodiment, (S)-Compound I-MsOH, e.g., synthesized by the disclosed process, will contain ≤0.25% of (R)-Compound I-MsOH. In one embodiment, (S)-Compound I-MsOH, e.g., synthesized by the disclosed process, will contain ≤0.20% of (R)-Compound I-MsOH.

In some embodiments, (S)-Compound I-MsOH, e.g., synthesized by the disclosed process, will contain ≤5.0% w/w water content as measured by U.S. Pharmacopeia (USP) <921>, method 1C. In some embodiments, (S)-Compound I-MsOH, e.g., synthesized by the disclosed process, will contain ≤2.5% w/w water content as measured by USP <921>, method 1C. In some embodiments, (S)-Compound I-MsOH, e.g., synthesized by the disclosed process, will contain ≤2.0% w/w water content as measured by USP <921>, method 1C. In some embodiments, (S)-Compound I-MsOH, e.g., synthesized by the disclosed process, will contain ≤1.0% w/w water content as measured by USP <921>, method 1C.

In some embodiments, (S)-Compound I-MsOH, e.g., synthesized by the disclosed process, will contain ≤20% w/w methanesulfonic acid. In some embodiments, (S)-Compound I-MsOH, e.g., synthesized by the disclosed process, will contain ≤15% w/w methanesulfonic acid. In some embodiments, (S)-Compound I-MsOH, e.g., synthesized by the disclosed process, will contain ≤13% w/w methanesulfonic acid. In some embodiments, (S)-Compound I-MsOH, e.g., synthesized by the disclosed process, will contain between about 5% to about 15% w/w methanesulfonic acid. In some embodiments, (S)-Compound I-MsOH, e.g., synthesized by the disclosed process, will contain between about 11% to about 13% w/w methanesulfonic acid.

In some embodiments, (S)-Compound I-MsOH, e.g., synthesized by the disclosed process, will contain ≤500 ppm acetonitrile as residual solvent. In some embodiments, (S)-Compound I-MsOH, e.g., synthesized by the disclosed process, will contain ≤425 ppm acetonitrile as residual solvent. In some embodiments, (S)-Compound I-MsOH, e.g., synthesized by the disclosed process, will contain ≤410 ppm acetonitrile as residual solvent. In some embodiments, (S)-Compound I-MsOH, e.g., synthesized by the disclosed process, will contain ≤350 ppm acetonitrile as residual solvent.

In some embodiments, (S)-Compound I-MsOH, e.g., synthesized by the disclosed process, will contain ≤7500 ppm ethyl acetate as residual solvent. In some embodiments, (S)-Compound I-MsOH, e.g., synthesized by the disclosed process, will contain ≤5000 ppm ethyl acetate as residual solvent. In some embodiments, (S)-Compound I-MsOH, e.g., synthesized by the disclosed process, will contain ≤4000 ppm ethyl acetate as residual solvent.

In some embodiments, (S)-Compound I-MsOH, e.g., synthesized by the disclosed process, will contain ≤300 ppm pyridine as residual solvent. In some embodiments, (S)-Compound I-MsOH, e.g., synthesized by the disclosed process, will contain ≤200 ppm pyridine as residual solvent. In some embodiments, (S)-Compound I-MsOH, e.g., synthesized by the disclosed process, will contain ≤100 ppm pyridine as residual solvent.

In some embodiments, (S)-Compound I-MsOH, e.g., synthesized by the disclosed process, will contain ≤750 ppm dichloromethane as residual solvent. In some embodiments, (S)-Compound I-MsOH, e.g., synthesized by the disclosed process, will contain ≤600 ppm dichloromethane as residual solvent. In some embodiments, (S)-Compound I-MsOH, e.g., synthesized by the disclosed process, will contain ≤500 ppm dichloromethane as residual solvent.

In some embodiments, (S)-Compound I-MsOH, e.g., synthesized by the disclosed process, will contain ≤1.0 ppm elemental impurities of cadmium as measured by USP <232> and/or ≤1.0 ppm lead. In some embodiments, (S)-Compound I-MsOH, e.g., synthesized by the disclosed process, will contain ≤0.5 ppm elemental impurities of cadmium as measured by USP <232> and/or ≤0.5 ppm lead. In some embodiments, (S)-Compound I-MsOH, e.g., synthesized by the disclosed process, will contain ≤0.25 ppm elemental impurities of cadmium as measured by USP <232> and/or ≤0.25 ppm lead.

In some embodiments, (S)-Compound I-MsOH, e.g., synthesized by the disclosed process, will contain ≤2.0 ppm elemental impurities of arsenic as measured by USP <232>. In some embodiments, (S)-Compound I-MsOH, e.g., synthesized by the disclosed process, will contain ≤1.5 ppm elemental impurities of arsenic as measured by USP <232>. In some embodiments, (S)-Compound I-MsOH, e.g., synthesized by the disclosed process, will contain ≤1.0 ppm elemental impurities of arsenic as measured by USP <232>.

In some embodiments, (S)-Compound I-MsOH, e.g., synthesized by the disclosed process, will contain ≤10.0 ppm elemental impurities of mercury as measured by USP <232> and/or ≤10.0 ppm cobalt. In some embodiments, (S)-Compound I-MsOH, e.g., synthesized by the disclosed process, will contain ≤5.0 ppm elemental impurities of mercury as measured by USP <232> and/or ≤5.0 ppm cobalt. In some embodiments, (S)-Compound I-MsOH, e.g., synthesized by the disclosed process, will contain ≤3.0 ppm elemental impurities of mercury as measured by USP <232> and/or ≤2.5 ppm cobalt. In one embodiment, (S)-Compound I-MsOH, e.g., synthesized by the disclosed process, will contain ≤2.0 ppm elemental impurities of mercury as measured by USP <232>. In one embodiment, (S)-Compound I-MsOH, e.g., synthesized by the disclosed process, will contain ≤2.0 ppm elemental impurities of cobalt as measured by USP <232>.

In some embodiments, (S)-Compound I-MsOH, e.g., synthesized by the disclosed process, will contain ≤20.0 ppm elemental impurities of vanadium as measured by USP <232> and/or ≤20.0 ppm palladium. In some embodiments, (S)-Compound I-MsOH, e.g., synthesized by the disclosed process, will contain ≤10.0 ppm elemental impurities of vanadium as measured by USP <232> and/or ≤10.0 ppm palladium. In some embodiments, (S)-Compound I-MsOH, e.g., synthesized by the disclosed process, will contain ≤5.0 ppm elemental impurities of vanadium as measured by USP <232> and/or ≤5.0 ppm palladium.

In some embodiments, (S)-Compound I-MsOH, e.g., synthesized by the disclosed process, will contain ≤30.0 ppm elemental impurities of nickel as measured by USP <232>. In some embodiments, (S)-Compound I-MsOH, e.g., synthesized by the disclosed process, will contain ≤20.0 ppm elemental impurities of nickel as measured by USP <232>. In some embodiments, (S)-Compound I-MsOH, e.g., synthesized by the disclosed process, will contain ≤10.0 ppm elemental impurities of nickel as measured by USP <232>.

In some embodiments, (S)-Compound I-MsOH, e.g., synthesized by the disclosed process, will contain ≤1500 ppm elemental impurities of chromium as measured by USP <232>. In some embodiments, (S)-Compound I-MsOH, e.g., synthesized by the disclosed process, will contain ≤1250 ppm elemental impurities of chromium as measured by USP <232>. In some embodiments, (S)-Compound I-MsOH, e.g., synthesized by the disclosed process, will contain ≤1100 ppm elemental impurities of chromium as measured by USP <232>. In one embodiment, (S)-Compound I-MsOH, e.g., synthesized by the disclosed process, will contain ≤1000 ppm elemental impurities of chromium as measured by USP <232>.

In some embodiments, (S)-Compound I-MsOH, e.g., synthesized by the disclosed process, will contain ≤500 ppm elemental impurities of molybdenum as measured by USP ≤232>. In some embodiments, (S)-Compound I-MsOH, e.g., synthesized by the disclosed process, will contain ≤300 ppm elemental impurities of molybdenum as measured by USP ≤232>. In one embodiment, (S)-Compound I-MsOH, e.g., synthesized by the disclosed process, will contain ≤250 ppm elemental impurities of molybdenum as measured by USP <232>.

EXAMPLES

Unless otherwise noted, the purity of the compounds was assessed using standard HPLC analysis. For example, a CAPCELL PAK® C18 column (Shisedo) with the dimensions of 4.6 cm×150 cm, 5 micron was used with a PDA 290 nm detector. The column temperature was set to 40° C., and the two mobile phases were A: 100% 0.05M $NH_4OAc$ in water and B: 100% acetonitrile. The flow rate was set at 1.0 mL/min with the run time of about 45-60 minutes per sample. The injection volume was 10 μL. In a different system, Clark instrument was used with PDA 293 nm detector. The injection volume was 20 μL and the run time was 120 minutes per sample.

Example 1

Optimization of Suzuki Coupling with $Pd(PPh_3)_4$ System

Table 1 describes the optimization efforts for the Suzuki coupling reaction using $Pd(PPh_3)_4$ catalyst system between Compound IV and Compound V-OMe. The reaction represented in Table 1 used Compound IV (5 g, 1 equiv), Compound V-OMe (2 equiv), and base (6.3 equiv) in solvent (ratio v/w with respect to Compound IV) and heated at reflux. This series of experiments show varying the reaction conditions did result in some reduction of impurity Compound VIII using the $Pd(PPh_3)_4$ system, although stalling or failure to recrystallize product was observed under most conditions.

TABLE 1

| Exp. # | Catalyst | Base Solvents (ratio) | Comments |
|---|---|---|---|
| 1 | $Pd(OAc)_2/PPh_3$ 2.0/8.0 mol % | $K_3PO_4$ THF:water (25:8) | 3 h: 50% conversion 6 h: 75% conversion Compound VIII: 0.25% |
| 2 | $Pd(PPh_3)_4$ 2.0 mol % | $K_3PO_4$ THF:water (25:8) | 4 h: 65% conversion Compound VIII: 0.135% |
| 3 | $Pd(OAc)_2/PPh_3$ 2.0/8.0 mol % | $K_3PO_4$ THF:water (25:8) | Grignard refluxed 27 h 4 h: 64% conversion Compound VIII: 0.22% |
| 4 | $Pd(OAc)_2/PPh_3$ 2.0/8.0 mol % | $K_3PO_4$ THF:water (25:8) | Using 1 equiv. boronic ester 8 h: 50% conversion Compound VIII: 0.11% |
| 5 | $Pd(OAc)_2/PPh_3$ 2.0/8.0 mol % | $K_3PO_4$ THF:water (25:8) | At 45° C. instead of refluxing 27 h: 100% conversion Compound VIII: 0.15% |
| 6 | $Pd(OAc)_2/PPh_3$ 10.0/40.0 mol % | $K_3PO_4$ THF:water (25:8) | 4 h: 100% conversion Compound VIII: 0.04% Trituration failed to produce crystals |

Example 2

Optimization of Suzuki Coupling with Pd Catalyst System

Table 2 outlines the optimization efforts for the Suzuki coupling reaction using $Pd(PPh_3)_4$ catalyst system between Compound IV and Compound V-OMe. The reaction represented in Table 2 used Compound IV (5 g, 1 equiv), Compound V-OMe (2 equiv), and base (6.3 equiv) in solvent (ratio v/w with respect to Compound IV) and heated at reflux. According to the results from Table 2, the $Pd(OAc)_2/P(o-tol)_3$ system uses significantly less catalyst, significantly less phosphine ligand and generally always proceeded to completion within 2 hours with no stalling observed, even without degassing. The $Pd(OAc)_2/P(o-tol)_3$ catalyst system produced Compound II-OH in increased yield and increased purity (>99%) when compared to the original $Pd(PPh_3)_4$ catalyst system. Additionally, this series of experiments also show varying the reaction conditions did not result in significant reduction of impurity Compound VIII compared with the $Pd(PPh_3)_4$ systems.

TABLE 2

| Exp. # | Catalyst | Base Solvents (ratio) | Comments |
|---|---|---|---|
| 1 | $Pd(OAc)_2$ 10.0 mol % | $K_2CO_3$ THF:water (25:8) | 27 h: 17% conversion Compound VIII: 0.15% |
| 2 | $Pd(dba)_2/PtBu_3$ 2.0/8.0 mol % | $K_3PO_4$ THF:water (25:8) | 4 h: 100% conversion Compound VIII: 0.15% Trituration failed to produce crystals |
| 3 | $Pd(OAc)_2/P(o-tol)_3$ 2.0/8.0 mol % | $K_2CO_3$ THF:water (25:8) | 2 h: 100% conversion Compound VIII: 0.08% Compound II-OH[2] > 99% purity |
| 4 | $Pd(OAc)_2/P(o-tol)_3$ 2.0/8.0 mol % | $K_2CO_3$ THF:water (25:8) | 1 h: 100% conversion Compound VIII: 0.06% Compound II-OH[2] > 99% purity |
| 5 | $Pd(OAc)_2/P(o-tol)_3$ 1.0/2.0 mol % | $K_2CO_3$ THF:water (25:8) | 100% conversion Compound VIII: 0.15% Compound II-OH[2] > 99% purity. |
| 6 | $Pd(OAc)_2/P(o-tol)_3$ 0.5/1.0 mol % | $K_2CO_3$ THF:water (25:8) | 1.5 h. 100% conversion Compound VIII: 0.13% Compound II-OH[2] > 99% purity |
| 7 | $Pd(OAc)_2/P(o-tol)_3$ 0.25/0.5 mol % | $K_2CO_3$ THF:water (25:8) | 2 h: 100% conversion Compound VIII: 0.17%, 0.38%[1] Compound II-OH[2] > 99% purity |
| 8 | $Pd(OAc)_2/P(o-tol)_3$ 0.25/0.5 mol % | $K_2CO_3$ THF:water (25:8) | Reaction was degassed for 4 h 2 h: 100% conversion Compound VIII: 0.28% Compound II-OH[2] > 99% purity |
| 9 | $Pd(OAc)_2/P(o-tol)_3$ 0.25/0.5 mol % | $K_2CO_3$ THF:water (25:8) | Reaction was not degassed 2 h: 100% conversion Compound VIII: 0.29% Compound II-OH[2] > 99% purity |

[1] Showing results of two different trials.
[2] Compound II-OH was triturated.

Example 3

Synthesis of Compound II-OH, with Recrystallization

Anhydrous tetrahydrofuran (THF, 9 parts) was added to magnesium (0.185 kg, 2.15 equiv) and the solution was stirred for 1 hour. THF was removed by distillation until the total volume of the solution was about 3 parts. To that, neat Compound VI (0.775 kg, 0.4 equiv) was added and the solution was heated to about 66° C. for 2 hours. The reaction was cooled to about 55° C. and additional anhydrous THF (5 parts) was added. To the hot solution, neat Compound VI (1.163 kg, 1.6 equiv) was added over 1 hour and the mixture was stirred at about 55° C. for about 4 hours to form the Grignard reagent. After HPLC analysis indicated less than about 1% of Compound VI was remaining, the reaction mixture was cooled to about −25° C. To the cooled reaction mixture, neat trimethoxyborane (0.739 kg, 2.0 equiv) was added portion-wise over 2 hours. The resulting mixture was stirred at −25° C. for 1 hour then warmed up to about 20° C. and stirred for 1 hour to yield Compound V-OMe.

To the reaction mixture containing Compound V-OMe, a solution of potassium carbonate (3.06 kg, 6.25 equiv) in water (5.5 parts) was portion-wise added over 1 hour. The biphasic solution was degassed with nitrogen for 1 hour then palladium acetate (0.002 kg, 0.0025 equiv) and tri-o-tolylphosphine (0.0054 kg, 0.0050 equiv) was added, while degassing continued. Subsequently, Compound IV (1.200 kg, 1.0 equiv) was added while degassing continued. The resulting reaction mixture was stirred at or below 65° C. for 4 hours or until HPLC analysis indicated ≤2% Compound IV was remaining. Once the reaction was deemed complete, it was cooled to an ambient temperature.

The reaction mixture was acidified using aqueous hydrochloric acid until the pH was adjusted to about 2.0-3.0. Once acidified, the layers were separated and the aqueous layer was extracted with toluene (10 parts). The combined organic layers were distilled to an approximate volume of 6.5 parts then Celite® (0.6 w/w, 0.720 kg) and Draco KBG (0.3 w/w, 0.360 kg, charcoal) were added and stirred for 3 hours at about 20° C. The charcoal and Celite® were removed by filtration and the filtrate was concentrated under reduced pressure to afford a volume of about 3 parts.

To the reduced solution, isopropanol (5 parts) was added and the mixture was again concentrated to a volume of 3 parts. To the resulting oil, heptanes (12 parts) were added portion-wise over 1 hour. The resulting suspension was stirred at about 20° C. for 6 hours and the crystals were collected by filtration.

The crude crystals collected by the filtration were then dissolved in ethyl acetate (0.4 parts) and isopropanol (3.6 parts) at 70° C. The temperature of the solution was reduced by 10° C. every 1 hour until the temperature reached 20° C. The solution was stirred at 20° C. for 4 hours and the crystals were collected by filtration and washed with heptanes. Compound II-OH was dried to yield 0.938 kg of yellow solid (58.5% yield, 99.42% purity).

HPLC purity method:
Column: CAPCELL PAK® C18, Shisedo, 4.6×150 cm, 5 micron
Detector wavelength: PDA 290 nm
Column temperature: 40° C.
Mobile phase: A: 100% 0.05M $NH_4OAc$ in water
B: 100% ACN
Run time: 45 minutes.
Injection volume: 10 µL Gradient Table:

| Time (min) | % A | % B |
|---|---|---|
| 0 | 90 | 10 |
| 5 | 90 | 10 |
| 8 | 10 | 90 |
| 10 | 10 | 90 |
| 11.01 | 90 | 10 |
| 20 | 90 | 10 |

Compound VI=8.3 minute

Compound V=2.3-2.6 minutes (three species in the mixture: Compound V-(OMe)2,

Compound V-(OMe)($Ar_1$), and Compound V-($Ar_1$)($Ar_2$))

Compound IV=3.0 minute

Compound II-OH=8.3 minute; purity=99.42%.

Example 4

Synthesis of Compound II-OH, with In Situ Generated Compound V Versus Crystalline, Isolated Compound V-OH To the reaction mixture containing either a) 2.0 equiv of in situ solution of Compound V-OMe or b) 2.0 equiv solution of Compound V-OH in water/THF prepared by dissolving isolated and crystalline Compound V-OH in water/THF, a solution of potassium carbonate (3.03 g, 6.25 equiv) in water (5.5 parts) was portion-wise added over 1 hour. The biphasic solution was degassed with nitrogen for 1 hour then palladium acetate (0.002 g, 0.0025 equiv) and tri-o-tolylphosphine (0.0045 g, 0.0050 equiv) was added, while degassing continued. Subsequently, Compound IV (1.00 g, 1.0 equiv) was added while degassing continued. The resulting reaction mixture was stirred at or below 65° C. for 4 hours or until HPLC analysis indicated ≤2% Compound IV was remaining. Once the reaction was deemed complete, it was cooled to an ambient temperature.

The reaction mixture was acidified using aqueous hydrochloric acid until the pH was adjusted to about 2.0-3.0. Once acidified, the layers were separated and the aqueous layer was extracted with toluene (10 parts). The combined organic layers were distilled to an approximate volume of 6.5 parts then Celite® (0.6 w/w, 0.600 kg) and Draco KBG (0.3 w/w, 0.300 g, charcoal) were added and stirred for 3 hours at about 20° C. The charcoal and Celite® were removed by filtration and the filtrate was concentrated under reduced pressure to afford a volume of about 3 parts.

To the reduced solution, isopropanol (5 parts) was added and the mixture was again concentrated to a volume of 3 parts. To the resulting oil, heptanes (12 parts) were added portion-wise over 1 hour. The resulting suspension was stirred at about 20° C. for 6 hours and the crystals were collected by filtration. Compound II-OH was dried to yield a yellow solid (Table 3 shows yield, purity and related substances). The HPLC condition from Example 3 was used to assess the purity represented in Table 3.

TABLE 3

| Condition | In situ Generated Compound V-OMe | Crystalline, Isolated Compound V-OH |
|---|---|---|
| Yield (%) of Compound II-OH | 70 | 67 |
| Product Analysis by HPLC | | |
| Compound IV-OH (% area) | 0.01 | 0.00 |
| Compound II-OH-A (% area) | 0.07 | 0.00 |
| Compound II-OH-B (% area) | 0.05 | 0.00 |
| Compound II-OH (% area) | 99.21 | 99.71 |
| Compound II-OH-C (% area) | 0.16 | 0.06 |
| Compound VIII (% area) | 0.10 | 0.00 |

Table 3 indicates that using crystalline, isolated compound V-OH in reaction with Compound IV reduced the impurities, namely Compound IV-OH, Compound II-OH-A, Compound II-OH-B, Compound II-OH-C, and Compound VIII. In particular, the presence of Compound IV-OH, Compound II-OH, Compound OH-B, and Compound VIII were reduced below detection. Further, the presence of Compound II-OH-C was also significantly reduced from 0.16% to 0.06%.

Previous synthesis utilized in situ solution of Compound V-OMe in reaction with Compound IV to prepare Compound II-OH. This reaction produced impurities of Compound IV-OH, Compound II-OH-A, Compound II-OH-B, Compound II-OH-C, and/or Compound VIII, which were very difficult to eliminate and necessitating multiple recrystallization purifications in order to provide Compound II-OH that met the impurity specifications. See, e.g., WO 2016/105527, the contents of this publication are herein incorporated by reference in their entirety for all intended purposes.

Thus, by substituting in situ solution of Compound V-OMe with a solution prepared from a crystalline and isolated Compound V-OH significantly reduced the purification process for Compound V-OH. In some embodiment, only one purification step is required when using crystalline and isolated Compound V-OH in reaction with Compound IV. In one embodiment, the purity of Compound II-OH is higher when prepared from crystalline and isolated Compound V-OH in reaction with Compound IV when compared from the purity of Compound II-OH prepared from in situ solution of Compound V-OMe in reaction with Compound IV.

In one embodiment, Compound II-OH prepared from crystalline, isolated Compound V-OH has about ≤0.01% of Compound II-OH-A, about ≤0.01% of Compound II-OH-B, and/or about ≤0.10% of Compound II-OH-C. In another embodiment, Compound II-OH prepared from crystalline, isolated Compound V-OH has about ≤0.01% of Compound II-OH-A, about ≤0.01% of Compound II-OH-B, and about ≤0.10% of Compound II-OH-C.

Example 5

Compound V-OH and Compound V-3

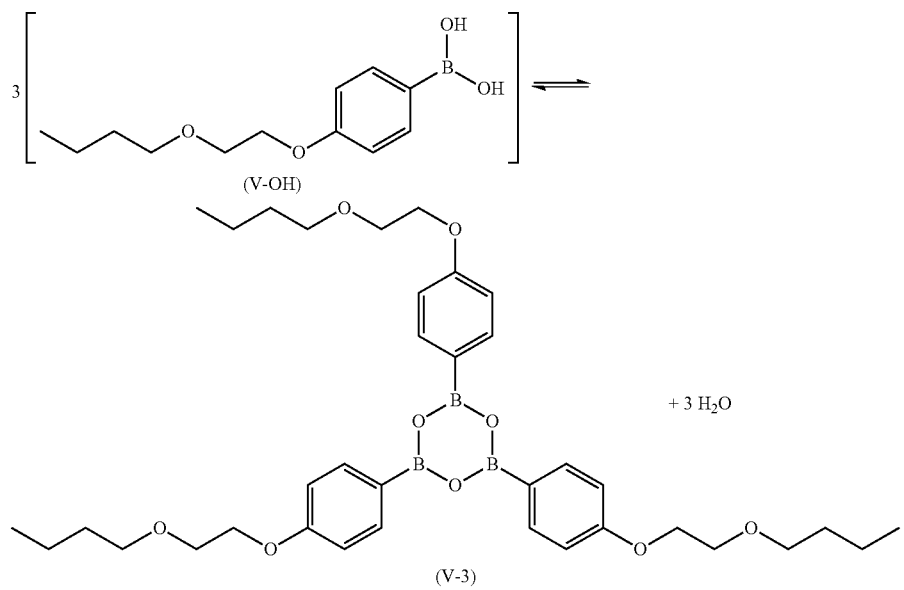

Figure 2:
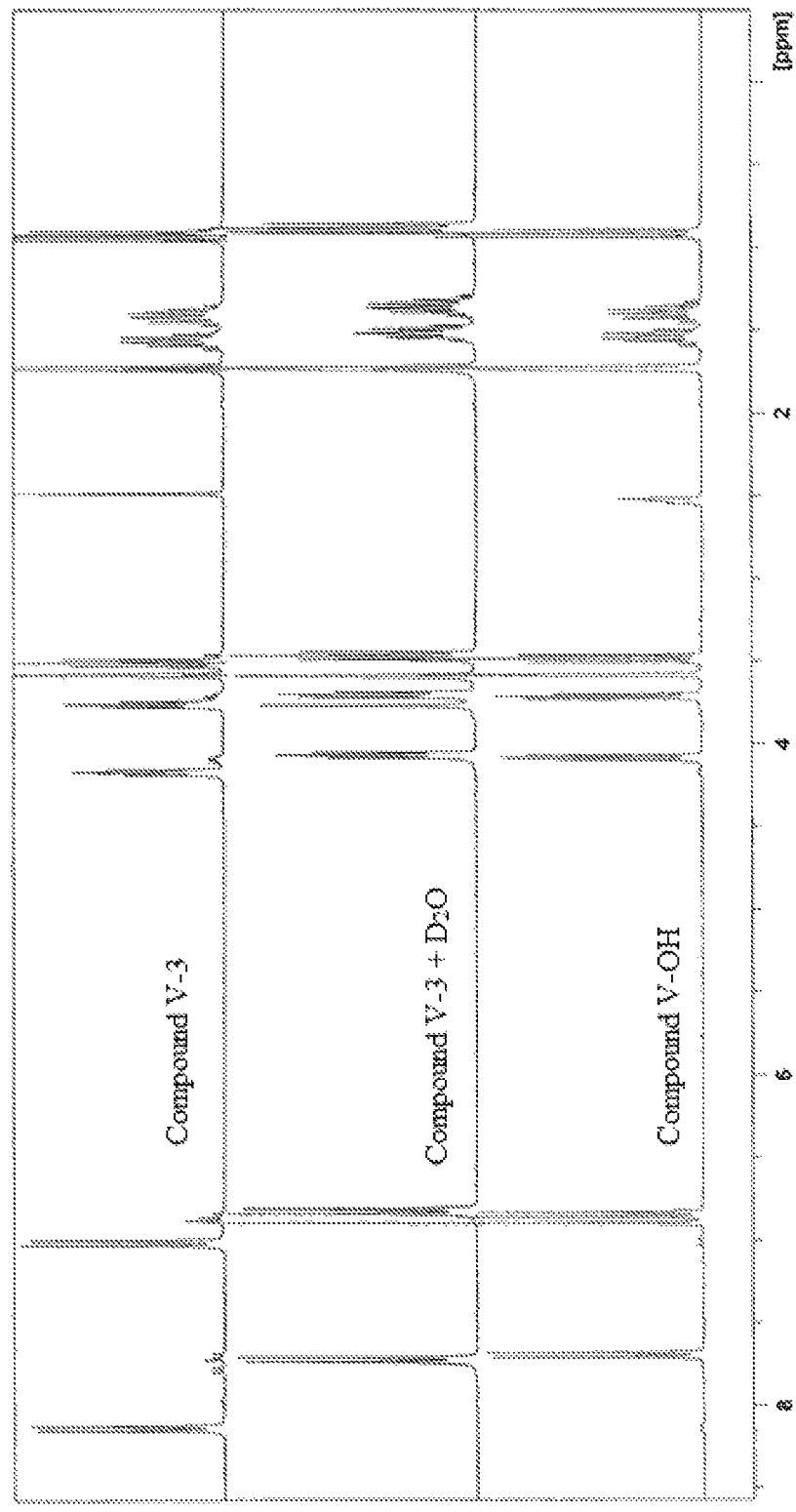
FIG. 2. shows a proton NMR spectra of Compound V-3 (top), Compound V-3 with $D_2O$ (middle), and Compound II-OH (bottom).
Figure 3:
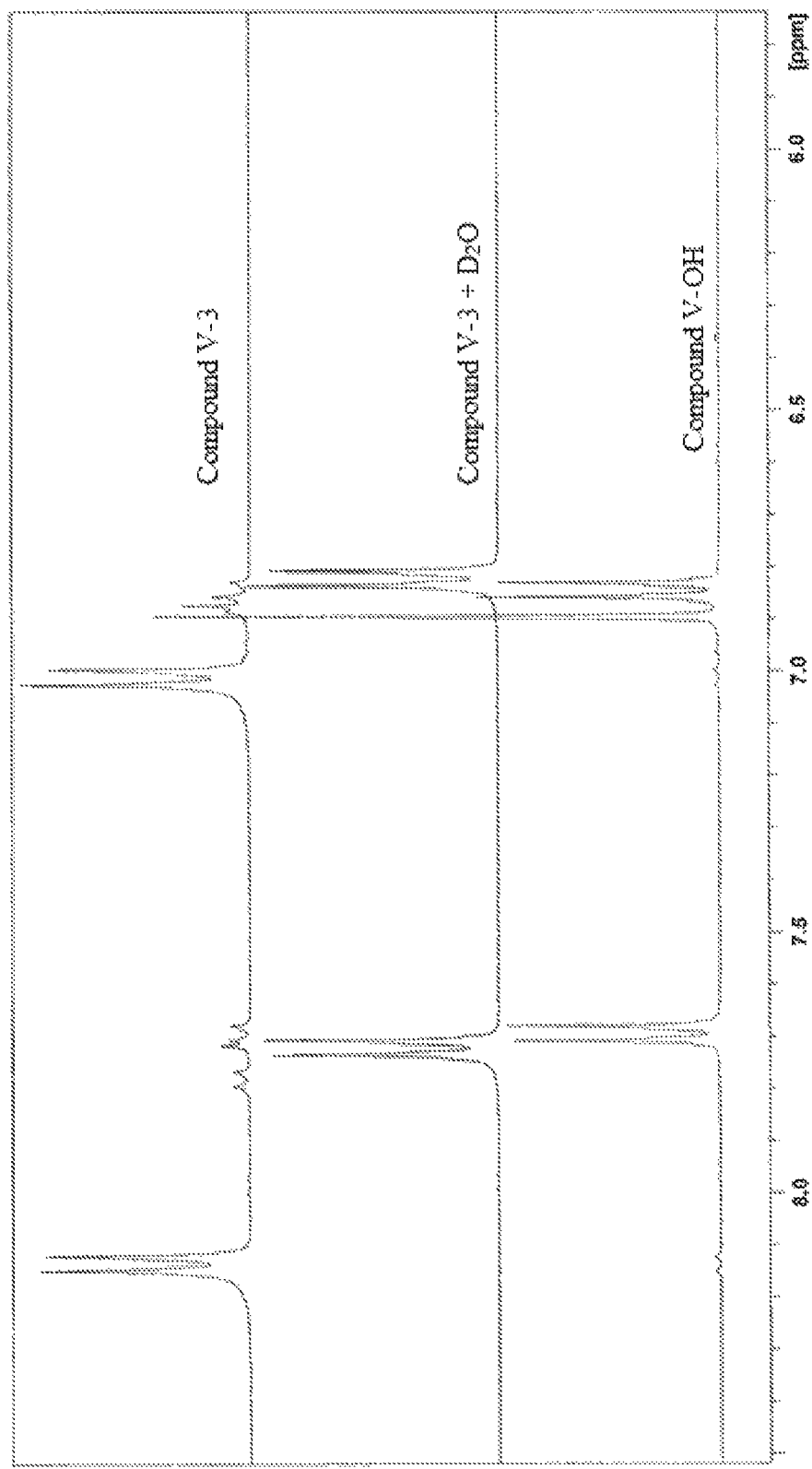
FIG. 3. shows an expansion of the aromatic region of the NMR spectra of FIG. 2.

Compound V-3 was formed during prolonged drying of Compound V-OH at higher temperatures, resulting in loss of water. Compound V-3 formation was observed when Compound V-OH was subject to drying to achieve loss on drying (LOD) below about 0.5%. As shown in FIG. 2, Compound V-3 (top spectrum) is characterized by a $^1$H NMR doublet in the 8.1-8.2 ppm region whereas Compound V-OH (bottom spectrum) is characterized by $^1$H NMR doublet in the 7.8-7.6 ppm region. FIG. 3 shows the aromatic region of the $^1$H NMR spectra of FIG. 2. The conversion of Compound V-3 to Compound V-OH in the presence of water was observed when $D_2O$ is added to the $^1$H NMR sample of Compound V-3 (FIG. 2, middle spectrum).

As demonstrated above, Compound V-3 readily converts to Compound V-OH under aqueous conditions, thus, in one embodiment, Compound V-3 and Compound V-OH can be used interchangeably or as a mixture in the reaction with Compound IV to prepare Compound II-OH. In one embodiment, when Compound V-3 is used in the reaction with Compound IV, about one third molar equivalence (compared to Compound V-OH) is necessary.

Example 6

Synthesis of Compound I-MsOH

Compound II-OH (34.7 kg, 1.0 equiv) was dissolved in dichloromethane (5 parts) and cooled to about 10-15° C. Neat thionyl chloride (10.1 kg, 1.10 equiv) was added portion-wise over 10 minutes and the mixture was stirred at about 10-15° C. for 3 hours. After HPLC analysis indicated ≤3% Compound II-OH was remaining, the reaction mixture was cooled to 0° C. A solution of (S)-Compound III (21.2 kg, 1.05 equiv) and pyridine (21.3 kg, 3.5 equiv) in dichloromethane (6 parts) was separately prepared and cooled to 0° C. To the solution of (S)-Compound III, the acid chloride solution was slowly added at 0° C. and stirred for 5 hours.

Upon completion of the reaction as indicated by HPLC analysis showing Compound II-Cl is ≤0.5%, a chilled solution of citric acid (27.7 kg, 1.7 equiv) in water (10 parts) was added over 30 minutes while maintaining an internal temperature of 0° C. Dichloromethane was removed under reduced pressure to a total volume of about 13 parts then ethyl acetate (5 parts) was added and the volume was again reduced under pressure to about 13 parts. The resulting residue was extracted with ethyl acetate (10 parts) and the organic layer was washed with aqueous solution of sodium bicarbonate (41.7 kg, 6.45 equiv) in water (10 parts) and the wash was repeated. The organic layer is further washed with brine (10 parts).

To the resulting organic layer was added 3 Å powdered molecular sieves (100% w/w, 34.8 kg) and the slurry was stirred for 20 hours then filtered. The filter cake was washed with ethyl acetate (2 parts). The dried organic layer containing Compound I was assayed by HPLC to determine the amount present. To the solution, acetonitrile (4 parts) was added then methanesulfonic acid (6.9 kg, 1.01 equiv) was added in one portion. Ethyl acetate (1 part) was used to transfer all of the methane sulfonic acid. The mixture was stirred at 20° C. for about 30 minutes.

The reaction mixture was then seeded with (S)-Compound I-MsOH and the mixture was stirred at 20° C. for 8 hours. The precipitated crystals were collected by filtration and washed with chilled ethyl acetate (1 part). The crude crystals were dissolved in acetonitrile (10 parts) at 70° C. and the solution was cooled to 50-55° C. over 1 hour and seeded with (S)-Compound I-MsOH. The solution was stirred at 50-55° C. for 6 hours then cooled to 20° C. over 1 hour then stirred for 8 hours. The precipitated crystals were collected by filtration and washed twice with chilled acetonitrile (2.5 parts each). The crystals were dried to provide 47.72 kg of (S)-Compound I-MsOH as a bright yellow solid (78% yield, 99.10% purity). The dried crystals were then pulverized by a powder mill and jet mill to give the final product composition.

HPLC purity method:

Column: CAPCELL PAK® C18, Shisedo, 4.6×150 cm, 5 micron

Detector wavelength: PDA290 nm

Column temperature: 40° C.

Mobile phase: A: 100% 0.05M $NH_4OAc$ in water

B: 100% ACN

Flow rate: 1.0 mL/min

Run time: 60 minutes

Injection volume: 10 μL

Gradient Table:

| Time (min) | % A | % B |
|---|---|---|
| 0 | 55 | 45 |
| 20 | 55 | 45 |
| 25 | 95 | 5 |
| 48 | 95 | 5 |
| 50 | 55 | 45 |
| 60 | 55 | 45 |
| 61 | 55 | 45 |
| 62 | 55 | 45 |

Compound II-OH=18.54 min

Compound I/Compound I-MsOH=26.05

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as acknowledgment or any form of suggestion that they constitute valid prior art or form part of the common general knowledge in any country in the world.

What is claimed is:

1. A composition of 8-(4-(2-butoxyethoxy)phenyl)-1-isobutyl-1,2,3,4-tetrahydrobenzo[b]azocine-5-carboxylic acid (Compound II-OH), that comprises one or more of the following:

(a) about ≤0.50% to about ≥0.30% or about ≤0.01% of 8-(4-(2-ethoxyethoxy)phenyl)-1-isobutyl-1,2,3,4-tetrahydrobenzo[b]azocine-5-carboxylic acid (Compound II-OH-A);

(b) about ≤0.50% to about ≥0.30% or about ≤0.01% of 1-isobutyl-8-(4-(2-propoxyethoxy)phenyl)-1,2,3,4-tetrahydrobenzo[b]azocine-5-carboxylic acid (Compound II-OH-B);

(c) about ≤0.50% to about ≥0.30% of 4,4'-bis(2-butoxyethoxy)biphenyl (Compound VII); and (d) about ≤0.50% to about ≥0.30% or about ≤0.01% of 8,8'-(4-(2-butoxyethoxy)-1,3-phenylene)bis(1-isobutyl-1,2,3,4-tetrahydrobenzo[b]azocine-5-carboxylic acid) (Compound VIII); and optionally further comprises one or both of about ≤0.50% of 8-(4-butoxyphenyl)-1-isobutyl-1,2,3,4-tetrahydrobenzo[b]azocine-5-carboxylic acid (Compound II-OH-C); and about ≤0.50% of 8-(4-(2-butoxyethoxy)phenyl)-1-butyl-1,2,3,4-tetrahydrobenzo[b]azocine-5-carboxylic acid (Compound IX).

2. The composition of claim 1, that comprises one or both of:
   (a) about ≤0.50% to about ≥0.30% of Compound II-OH-A; and
   (b) about ≤0.50% to about ≥0.30% of Compound II-OH-B; and optionally further comprises about ≤0.50% of Compound II-OH-C.

3. The composition of claim 1, that comprises one or both of:
   (a) about ≤0.01% of Compound II-OH-A; and
   (b) about ≤0.01% of Compound II-OH-B; and optionally further comprises about ≤0.10% of Compound II-OH-C.

4. The composition of claim 1, that comprises one or both of:
   (a) about ≤0.50% to about ≥0.30% of Compound VII; and
   (b) about ≤0.50% to about ≥0.30% of Compound VIII; and optionally further comprises about ≤0.50% of Compound IX.

5. The composition of claim 1, that comprises about ≤0.01% of Compound VIII, and optionally further comprises one or both of
   about ≤0.05% of Compound VII, and
   about ≤0.15% of Compound IX.

6. The composition of claim 1, wherein the Compound II-OH has about >97.0% purity.

7. A composition comprising 8-(4-(2-butoxyethoxy)phenyl)-1-isobutyl-1,2,3,4-tetrahydrobenzo[b]azocine-5-carboxylic acid (Compound II-OH), with ≥95.0% to ≤96.0% purity.

8. The composition of claim 7, wherein 4,4'-bis(2-butoxyethoxy)biphenyl (Compound VII) is present in 0.20% or less.

9. The composition of claim 7, wherein 4,4'-bis(2-butoxyethoxy)biphenyl (Compound VII) is present in 0.10% or less; or 8,8'-(4-(2-butoxyethoxy)-1,3-phenylene)bis(1-isobutyl-1,2,3,4-tetrahydrobenzo[b]azocine-5-carboxylic acid) (Compound VIII) is present in 0.10% or less; or 8-(4-(2-butoxyethoxy)phenyl)-1-butyl-1,2,3,4-tetrahydrobenzo[b]azocine-5-carboxylic acid (Compound IX) is present in 0.15% or less.

10. The composition of claim 7, wherein said composition comprises one or more of the following:
   (a) 0.50% or less of 8-(4-(2-ethoxyethoxy)phenyl)-1-isobutyl-1,2,3,4-tetrahydrobenzo[b]azocine-5-carboxylic acid (Compound II-OH-A);
   (b) 0.50% or less of 1-isobutyl-8-(4-(2-propoxyethoxy)phenyl)-1,2,3,4-tetrahydrobenzo[b]azocine-5-carboxylic acid (Compound II-OH-B);
   (c) 0.50% or less of 8-(4-butoxyphenyl)-1-isobutyl-1,2,3,4-tetrahydrobenzo[b]azocine-5-carboxylic acid (Compound II-OH-C);
   (d) 0.50% or less of 8,8'-(4-(2-butoxyethoxy)-1,3-phenylene)bis(1-isobutyl-1,2,3,4-tetrahydrobenzo[b]azocine-5-carboxylic acid) (Compound VIII); and/or
   (e) 0.50% or less of 8-(4-(2-butoxyethoxy)phenyl)-1-butyl-1,2,3,4-tetrahydrobenzo[b]azocine-5-carboxylic acid (Compound IX).

11. The composition of claim 7, wherein said composition comprises one or more of the following:
   (a) 0.05% or less of 8-(4-(2-ethoxyethoxy)phenyl)-1-isobutyl-1,2,3,4-tetrahydrobenzo[b]azocine-5-carboxylic acid (Compound II-OH-A);
   (b) 0.05% or less of 1-isobutyl-8-(4-(2-propoxyethoxy)phenyl)-1,2,3,4-tetrahydrobenzo[b]azocine-5-carboxylic acid (Compound II-OH-B);
   (c) 0.05% or less of 8-(4-butoxyphenyl)-1-isobutyl-1,2,3,4-tetrahydrobenzo[b]azocine-5-carboxylic acid (Compound II-OH-C);
   (d) 0.05% or less of 8,8'-(4-(2-butoxyethoxy)-1,3-phenylene)bis(1-isobutyl-1,2,3,4-tetrahydrobenzo[b]azocine-5-carboxylic acid) (Compound VIII); and/or
   (e) 0.15% or less of 8-(4-(2-butoxyethoxy)phenyl)-1-butyl-1,2,3,4-tetrahydrobenzo[b]azocine-5-carboxylic acid (Compound IX).

12. The composition of claim 1, wherein 8-(4-(2-butoxyethoxy)phenyl)-1-isobutyl-1,2,3,4-tetrahydrobenzo[b]azocine-5-carboxylic acid (Compound II-OH) is prepared by:
   reacting (4-(2-butoxyethoxy)phenyl)boronic acid (Compound V-OH) with 8-bromo-1-isobutyl-1,2,3,4-tetrahydrobenzo[b]azocine-5-carboxylic acid;
   reacting 2,4,6-tris(4-(2-butoxyethoxy)phenyl)-1,3,5,2,4,6-trioxatriborinane (Compound V-3) with 8-bromo-1-isobutyl-1,2,3,4-tetrahydrobenzo[b]azocine-5-carboxylic acid; or
   reacting a mixture of (4-(2-butoxyethoxy)phenyl)boronic acid (Compound V-OH) and 2,4,6-tris(4-(2-butoxyethoxy)phenyl)-1,3,5,2,4,6-trioxatriborinane (Compound V-3) with 8-bromo-1-isobutyl-1,2,3,4-tetrahydrobenzo[b]azocine-5-carboxylic acid.

13. The composition of claim 12, wherein (4-(2-butoxyethoxy)phenyl)boronic acid (Compound V-OH) is a crystalline form of Compound V-OH.

14. The composition of claim 12, wherein 2,4,6-tris(4-(2-butoxyethoxy)phenyl)-1,3,5,2,4,6-trioxatriborinane (Compound V-3) is a crystalline form of Compound V-3.

15. The composition of claim 12, that comprises one or both of:
   (a) about ≤0.01% of Compound II-OH-A; and
   (b) about ≤0.01% of Compound II-OH-B; and optionally further comprises about ≤0.10% of Compound II-OH-C.

16. The composition of claim 12, that comprises:
   (a) about ≤0.01% of Compound II-OH-A;
   (b) about ≤0.01% of Compound II-OH-B; and
   (c) about ≤0.10% of Compound II-OH-C.

* * * * *